(12) United States Patent
Swenson

(10) Patent No.: US 9,663,511 B2
(45) Date of Patent: May 30, 2017

(54) SPHINGOSINE 1-PHOSPHATE RECEPTOR ANTAGONISTS

(71) Applicant: ARROYO BIOSCIENCES, LLC, Silver Spring, MD (US)

(72) Inventor: Rolf E. Swenson, Silver Spring, MD (US)

(73) Assignee: Arroyo BioSciences, LLC, Silver Spring, MD (US)

( * ) Notice: Subject to any disclaimer, the term of this patent is extended or adjusted under 35 U.S.C. 154(b) by 0 days.

(21) Appl. No.: 14/386,990

(22) PCT Filed: Mar. 21, 2013

(86) PCT No.: PCT/US2013/033289
§ 371 (c)(1),
(2) Date: Sep. 22, 2014

(87) PCT Pub. No.: WO2013/148460
PCT Pub. Date: Oct. 3, 2013

(65) Prior Publication Data
US 2015/0045332 A1    Feb. 12, 2015

Related U.S. Application Data

(60) Provisional application No. 61/615,454, filed on Mar. 26, 2012.

(51) Int. Cl.
C07D 471/04 (2006.01)
A61K 31/444 (2006.01)
A61K 31/437 (2006.01)
A61K 45/06 (2006.01)

(52) U.S. Cl.
CPC .......... *C07D 471/04* (2013.01); *A61K 31/437* (2013.01); *A61K 31/444* (2013.01); *A61K 45/06* (2013.01)

(58) Field of Classification Search
None
See application file for complete search history.

(56) References Cited

U.S. PATENT DOCUMENTS

| 6,943,180 | B2 | 9/2005 | Doherty et al. |
| 7,838,562 | B2 | 11/2010 | Hla et al. |
| 7,846,928 | B2 | 12/2010 | Hartung et al. |
| 7,910,626 | B2 | 3/2011 | Brinkmann et al. |
| 8,114,902 | B2 | 2/2012 | Kiuchi et al. |
| 2004/0058894 | A1 | 3/2004 | Doherty et al. |
| 2009/0004207 | A1 | 1/2009 | Hla et al. |
| 2010/0068200 | A1 | 3/2010 | Hla et al. |
| 2011/0015159 | A1 | 1/2011 | Hla et al. |

FOREIGN PATENT DOCUMENTS

WO    WO 01/98301    12/2001

OTHER PUBLICATIONS

Byrn, Stephen. Solid-State Chemistry of Drugs, 2nd Ed. (1999), Ch. 11 Hydrates and Solvates, 233-247.*
Morissette, Sherry. Adv. Drug Delivery Rev. 2004, 56, 275-300.*
Rouhi, A. Maureen. Chem. & Eng. News, (2003), 81(8), 32-35.*
Rosen, Hugh. Annu. Rev. Biochem. 2009. 78: 743-68.*
Rivera, Juan. Nature Reviews: Immunology. vol. 8 (2008) 753-763.*
Nall, Rachel. Healthline. Pulmonary Fibrosis: Definition and Patient Education. (2016) Web <http://www.healthline.com/health/pulmonary-fibrosis>.*

* cited by examiner

*Primary Examiner* — Golam M M Shameem
*Assistant Examiner* — Laura Daniel
(74) *Attorney, Agent, or Firm* — Saul Ewing LLP; Domingos J. Silva

(57) ABSTRACT

The present invention relates to sphingosine-1-phosphate (S1P) receptors and compounds of the general formula:

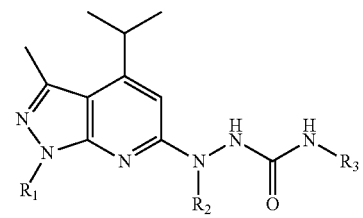

that are useful in the treatment and prevention of conditions associated with such receptors. More specifically, the present invention relates to the synthesis and use of sphingosine 1-phosphate receptor 2 ($S1P_2$) antagonists that are useful in the treatment of cancer, atherosclerosis, diabetic retinopathy, and other inflammatory diseases. Among these inflammatory diseases that could be treated with these $S1P_2$ antagonist are those characterized by fibrosis including chronic lung disease, chronic kidney and liver disease, chronic heart disease, and skin diseases such as sclerosis/scleroderma. The $S1P_2$ antagonists can also be used in the treatment of glioblastoma multiforme (brain cancer), pediatric neuroblastoma, and other cancers.

14 Claims, 5 Drawing Sheets

SPHINGOSINE 1-PHOSPHATE RECEPTOR ANTAGONISTS

CROSS-REFERENCE TO RELATED APPLICATIONS

The present application is a 35 U.S.C. §371 national phase application from, and claims priority to, International Application No. PCT/US2013/033289, filed Mar. 21, 2013, and published under PCT Article 21(2) in English, which claims priority under 35 U.S.C. §119(e) to U.S. Provisional Application No. 61/615,454, filed Mar. 26, 2012, all of which applications are incorporated herein by reference in their entireties.

FIELD OF THE INVENTION

The present invention relates to sphingosine-1-phosphate (S1P) receptors and compounds used in the treatment and prevention of conditions associated with such receptors. More specifically, the present invention relates to the synthesis and biological testing of new derivatives of JTE013, a known sphingosine 1-phosphate receptor 2 ($S1P_2$) antagonist. $S1P_2$ antagonists have the potential to be used in cancer, in atherosclerosis, diabetic retinopathy and in other inflammatory diseases. Among these inflammatory diseases that could be treated with an $S1P_2$ antagonist are those characterized by fibrosis including chronic lung disease, chronic kidney and liver disease, chronic heart disease, and skin diseases such as sclerosis/scleroderma. The $S1P_2$ antagonists can also be used in the treatment of glioblastoma multiforme (brain cancer), pediatric neuroblastoma, and other cancers.

BACKGROUND OF THE INVENTION

Receptor antagonists are chemical compounds that act as cellular receptor ligands that do not provoke a biological response upon binding to a receptor, but block or dampen agonist-mediated responses. In pharmacology, antagonists have affinity but no efficacy for their cognate receptors, and binding thereto will disrupt the interaction and inhibit the function of an agonist or inverse agonist at the receptor site. Antagonists mediate their effects by binding to the active site or to allosteric sites on receptors, or they may interact at unique binding sites not normally involved in the biological regulation of the cellular receptor's activity. Antagonist activity may be reversible or irreversible depending on the longevity of the antagonist-receptor complex, which, in turn, depends on the nature of antagonist receptor binding. The majority of drug antagonists achieve their potency by competing with endogenous ligands or substrates at structurally-defined binding sites on receptors. Angiogenesis is directly involved in a number of pathological conditions such as tumor growth, inflammation and diabetic retinopathy. Current approaches to the treatment of abnormal angiogenesis in the eye include laser therapy, which destroys some retinal tissue in order to preserve some vision, and the administration of anti-VEGF antibody and/or anti-VEGF RNA aptomer. There remains a clear need for improved methods and agents for prevention and treatment of conditions involving abnormal angiogenesis and harmful pathological angiogenesis in the tissues of the eye Sphingosine 1-phosphate (S1P) is a lipid mediator that regulates various biological processes, such as cell proliferation, migration, survival and differentiation. S1P which is generated by the phosphorylation of sphingosine by sphingosine kinase 1 (Sphk1) and sphingosine kinase 2 (Sphk2), is degraded by S1P-specific phosphatases and a lyase. It is a ligand with high affinity for five (5) G-protein coupled S1P receptors on the cell-surface, $S1P_{1R}$, $S1P_{2R}$, $S1P_{2R}$, $S1P_{4R}$ and $S1P_{5R}$, that regulate distinct intracellular signaling pathways. $S1P_1$, $S1P_2$ and $S1P_3$ receptors are widely expressed, whereas $S1P_4$ and $S1P_5$ expression is prominent in cells of the immune and nervous systems, respectively. The $S1P_1$ receptor couples exclusively to $G_i$ signaling pathway, whereas $S1P_2$ and $S1P_3$ receptors couple to Gi as well as to the Gq and $G_{12/13}$ pathways. However, $S1P_2$ activates $G_{12/13}$ potently, whereas $S1P_3$ activates Gq preferentially.

FTY720 is a potent immuno-modulator that has a mechanism of action which includes phosphorylation into FTY720-P, which is an agonist for four of the five S1P receptors in T lymphocytes. It was shown previously that FTY720 is a potent modulator of lymphocyte trafficking, however, the effect of FTY720 on vascular elements was previously unknown.

It has been demonstrated that vascular endothelial cells contain enzyme systems that "activate" FTY720 and its analogs. Cultured endothelial cells such as human umbilical vein endothelial cells (HUVEC) are accepted in in vitro model systems for studying angiogenesis. Upon incubation with HUVEC conditioned medium or cell extracts, FTY720 is phosphorylated and is able to activate the endothelial cells to migrate in a pertussis-toxin sensitive manner, suggesting that it is activating the Gi-coupled S1P receptors. It is shown herein that endothelial cell-derived sphingosine kinase-2 (SK2) is involved in the activation of FTY720 into FTY720-P.

S1P receptors also regulate important physiological functions of the vascular system, such as vascular morphogenesis and maturation, cardiac function, vascular permeability and tumor angiogenesis. Indeed, $S1P_1$ null embryos die due to massive hemorrhage at E 12.5-14.5 days of gestation since the $S1P_1$ receptor is essential for proper stabilization of the embryonic vascular system by promoting the formation of strong N-cadherin-based junctions between endothelial and vascular smooth muscle cells. However, mice that lack either the $S1P_2$ or the $S1P_3$ receptor are viable and fertile.

Interestingly, $S1P_1/S1P_2$ double null embryos showed a more severe phenotype than $S1P_1$ single null embryos, suggesting that $S1P_2$ receptor is also significant during embryonic vascular development. In addition, $S1P_2$ null mice are profoundly deaf due to vascular abnormalities in the stria vascularis of the inner ear and degeneration of sensory hair cells of the organ of Corti. Moreover, a mutation in the zebrafish gene miles-apart (Mil), an $S1P_2$ analog, results in cardiac developmental defects (cardia bifida) due to the defective migration of cardiomyocyte precursors, underscoring the significance of this receptor for the fish cardiac development. However, the role of the $S1P_2$ receptor in vascular development and pathology is an active area of study.

The process of forming new blood vessels is termed angiogenesis. During angiogenesis, vascular endothelial cells undergo orderly proliferation, migration, and morphogenesis to form new capillary networks. Under normal or non-pathologic conditions, angiogenesis occurs under well-defined conditions such as in wound healing, tissue and cellular response to ischemia, and during embryonal and fetal development. However, persistent or uncontrolled angiogenesis can lead to a variety of disease states or conditions and, in the case of solid tumors, may be a necessary condition to maintain the disease state.

U.S. Pat. No. 7,838,562 to Hla et. al. discloses and claims a number of agonist compounds of vascular endothelial sphingosine-1-phosphate receptors that are asserted to be useful in the treatment of vascular permeability disorders, comprising the administration of a therapeutically effective amount of a compound selected from the group comprising 2-amino-2-[2-(4-octaphenyl)ethyl]propane-1,3 diol, or 2-amino-2-methyl-4-[4-heptoxy-phenyl]butane-1-ol. The vascular permeability disorder may be any one associated with endothelial injury, thrombocytopenia, ischemic peripheral vascular disease, any one of a number of peripheral vascular disorders associated with diabetes, Dengue hemorrhagic fever, acute respiratory distress syndrome, vascular leak syndrome, or a combination thereof. The afore-mentioned compounds can be phosphorylated by sphingosine kinase-2 into the phosphorylated forms which serve as sphingosine-1-phosphate receptor agonists.

U.S. Pat. No. 7,910,626 to Brinkman et. al. discloses compounds for treating chronic or congestive heart failure comprising administering to said subject a therapeutically effective amount of 2-amino-2-[2-(4-octylphenyl)ethyl]propane-1,3-diol in free form or a pharmaceutically acceptable salt or phosphate thereof.

U.S. Pat. No. 8,114,902 to Kiuchi et. al. discloses and claims compounds useful in the treatment or prophylaxis of auto-immune diseases or acute and chronic rejection due to organ or tissue transplantation, graft vs host (GvH) disease due to bone marrow transplantation and the treatment or prophylaxis of allergic diseases. Particularly suitable compounds include the pharmaceutically acceptable acid addition salt, hydrate or a solvate of 2-amino-2-{2-[2'-fluoro-4'-(4-methylphenylthio)biphenyl-4-yl]ethyl}propane-1,3-diol and 2-amino-4-[2'-fluoro-4'-(4-methylphenylthio)biphenyl-4-yl]-2-(phosphoryloxymethyl) butanol.

U.S. Patent Appln. No. 2011/0015159 also to Hla et. al. discloses and claims a number of novel agonists of vascular endothelial sphingosine-1-phosphate receptors. Known compounds agonists such as FTY720 can be phosphorylated by sphingosine kinase-2 into the phosphorylated forms which serve as sphingosine-1-phosphate receptor agonists. These vascular endothelial receptor agonists can be formulated into pharmaceutical compositions for treating vascular permeability disorders and unwanted vascular endothelial cell apoptosis.

WO 01/98301 to Kawasaki et. al. relates to new pyrazolopyridine compounds having sphingosine-1-phosphate receptor antagonistic activity and their use in pharmaceutical compositions as fibrosis remedies that contain Sph-1-P receptor antagonistic activity or pharmaceutically acceptable salts as an active ingredient. Specifically, the invention relates to new compounds of the formula:

一般式 (1)

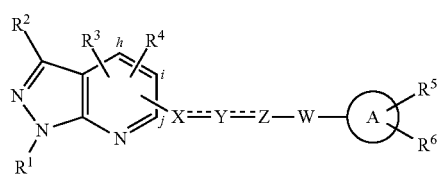

(1)

where in $R^1$, $R^2$ and $R^3$ are each $C_{1-8}$ alkyl and the like; $R^4$ is hydrogen and the like; $R^5$ and $R^6$ are each independently hydrogen, $C_{1-8}$ alkyl, $C_{1-6}$ alkoxy, halogen; X is NH—, —O—, —CH$_2$—, Y is NH—; Z is CO—; W is NH—; and A is aryl or heteroaryl, These compounds are asserted to have that have therapeutic efficacy for liver, kidney, and lung fibrosis or arteriosclerosis caused by thickening of vascular smooth muscle.

European patent application EP 1 424 078 A1 to S. Nakade et. Al discloses and claims a number of S1P antagonists as remedies for respiratory diseases comprising shingosine-1-phosphate receptor controller. These compounds can be used to treat or prevent airway constriction, bronchial asthma and chronic obstructive pulmonary disease (COPD), pulmonary emphysema, tracheostenosis, diffused panbronchialitis, or bronchitis with infection, connective-tissues diseases or transplantation, lymphangioleiomyomatosis, adult respiratory distress syndrome (ARDS), interstitial pneumonia, lung cancer, hypersensitive pneumonitis or idiopathic interstitial pneumonia.

WO 2011/048287 A1 to W. K. Fang et. al discloses and claims condensed ring pyridine compounds as subtype-selective modulators of sphingosine-1-phosphate-2 (S1P$_2$) receptors. These compounds can be used to treat or prevent diseases and conditions consisting of ocular diseases: cardiac diseases or conditions, fibrosis, pain and wounds.

U.S. Patent Appln. No. 2009/00004207 to Hla et. al. discloses and claims a number of novel agonists of vascular endothelial sphingosine-1-phosphate receptors. Known compounds agonists such as FTY720 can be phosphorylated by sphingosine kinase-2 into the phosphorylated forms which serve as sphingosine-1-phosphate receptor agonists. These vascular endothelial receptor agonists can be formulated into pharmaceutical compositions for treating vascular permeability disorders and unwanted vascular endothelial cells. Known agonists such as FTY720 can be phosphorylated by sphingosine kinase-2 into the phosphorylated forms which serve as sphingosine-1-phosphate receptor agonists. These vascular endothelial receptor agonists can be formulated into pharmaceutical compositions for treating vascular permeability disorders and unwanted vascular endothelial cell tumors.

U.S. Patent Appln. No. 2011/041287 also to Hla et al discloses a number of compounds that inhibit abnormal angiogenesis in the eye, particularly in the retina. The compounds are asserted to be effective inhibitors of the receptor activity of the S1P$_2$ receptor. The compositions include the S1P$_2$ receptor antagonist and an opthalmically acceptable excipient.

In order to determine the role of the S1P$_2$ receptor in mammalian vascular development, the retinal vascular development of mice lacking the S1P$_2$ receptor was examined under physiological (normal retina development) and patho-physiological conditions (ischemic-driven retinopathy). Post-natal vascular development of the mouse retina provides an attractive model system to explore the mechanisms of angiogenesis and vascular stabilization. After birth, endothelial cells emerge from the optic disc and form the primary vasculature of the mouse retina. Vessels that grow with radial orientation are formed along the retina neuronal and astrocytic plexus. On the other hand, pathological retina angiogenesis produces abnormally growing and chaotically oriented dysfunctional vessels that grow into the vitreous fluid as "vascular tufts" and eventually lead to vision loss. This phenotype is common in the pediatric retinopathy of prematurity (ROP) and in diabetic retinopathy of the adult.

It has been shown that the angiogenic process proceeds normally in S1P$_{-/-2}$ mice during normal retinal development. However, when mice were exposed to ischemic stress, S1P$_{2-/-}$ retinas appear to have increased "physiological" intra-retinal angiogenesis and reduced "pathological" intra-vitreal neo-vascularization. It was further demonstrated that the S1P$_2$ receptor is required for inflammatory cell infiltration, induction of the pro-inflammatory and pro-angiogenic enzyme cyclo-oxygenase (COX)-2 and the suppression of the endothelial nitric oxide synthase (eNOS) which produces the vasodilator nitrous oxide (NO). This study identified S1P signaling by the S1P$_2$ receptor as a novel target for the prevention and/or treatment of vision-threatening retinopathies.

In a paper by Schwalm Pfeilschifter and Huwiler (Biochimica et Biophysica Acta 1831 (2013) 239-250) the general effects of extracellular and intracellular S1P on the multi-step cascade of pathological fibrogenesis including tissue injury, inflammation and the action of pro-fibrotic cytokines that stimulate ECM production and deposition is examined, The current knowledge about the involvement of S1P is suggested as being involved in the control of signaling in the development of organ fibrosis of the lung, kidney, liver, heart and skin. It is further shown that targeting the sphingosine kinase-1/S1P signaling pathway offers therapeutic potential in the treatment of various fibrotic processes.

In one embodiment of the present invention, a method of treating abnormal angiogenesis in the eye comprises administering to an individual in need thereof an effective amount of an S1P$_2$ receptor antagonist. As used herein, the term "treating" includes the administration to an individual suffering from abnormal angiogenesis of the eye as well as the administration, both preventatively or prophylactically to an individual at risk of abnormal angiogenesis of the eye. Administration of an S1P$_2$ receptor antagonist to an individual at risk for abnormal angiogenesis of the eye can prevent abnormal angiogenesis of the eye. In one embodiment, the individual is at risk of, or has been diagnosed with, abnormal angiogenesis of the eye.

In another embodiment of the invention, the method of treatment involves the pathological angiogenesis in the eye associated with an ocular neo-vascular disease. This type of disease is characterized by invasion of new blood vessels into the structures of the eye such as the retina or cornea. It is the most common cause of blindness and is involved in approximately twenty (20) eye diseases. In age-related macular degeneration, the associated visual problems are caused by an in-growth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retro-lental fibroplasia. Other diseases associated with corneal neo-vascularization include, but are not limited to, epidemic kerato-conjunctivitis, Vitamin A deficiency, contact lens over-wear, atopic keratitis, superior limbic keratitis, pterygium keratitis sicca, sjogrens disease, acne rosacea, phylectenulosis, syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Other diseases associated with retinal/choroidal neo-vascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacterial infections, lyme disease, systemic lupus erythematosis, infant retinopathy, Eales' disease, Behcet's disease, retinitis or choroiditis caused by bacterial or viral infection, presumed ocular histoplasmosis, Best's disease, myopia, optic pits, Stargardt's disease, pars planatitis, chronic retinal detachment, hyper-viscosity syndromes, toxoplasmosis, trauma and post-laser complications. Other eye-related diseases include, but are not limited to, diseases associated with rubeosis (neovascularization of the eye) and diseases caused by the abnormal proliferation of fibrovascular or fibrous tissue, including all forms of prolific vitreo-retinopathy.

In another embodiment, pathological angio-genesis of the eye is associated with a neoplastic eye disease. Neoplastic eye diseases include primary ocular tumors, such as uveal melanomas, melanocytomas, retinocytomas, retinal hematomas and choristomas, retinal angiomas, retinal gliomas and astocytomas, choroidal hemangiomas, choroidal neurofibromas, choroidal hematomas and choristomas, ocular lymphomas and ocular phakomatoses; and metastatic ocular tumors related to choroidal and retinal neo-vascularization. Similar to the non-neoplastic diseases, the above tumors also share the retinal neovascularization as a key component.

Pathological angiogenesis and several types of inflammatory disease have been correlated with increased S1P$_2$ receptor levels. JTE013 is the only currently available S1P$_2$ receptor selective antagonist compound. However, the anecdotal reports have confirmed that JTE013 has very poor in vivo characteristics, based at least in part on its rapid metabolic clearance. These characteristics limit the efficacy and usefulness of JTE013 in treating and preventing sphingosine-1-phosphate-mediated diseases and disorders.

Ferrer and Hla have reported that neuroblastoma cell lines over-express S1P$_2$ receptors, and suggest that S1P$_2$ antagonists could be used for this pediatric cancer. Van Brocklyn and Young, and others have shown the importance of S1P$_2$ receptors in the morphology of cellular invasiveness and its' proliferation in glioma cells (which are responsible for glioblastoma multiforme).

JTE013 is a well known sphingosine 1-phosphate receptor 2 (S1P$_2$) class of antagonists that have the potential to be useful as anti-angiogenesis agents in cancer, atherosclerosis, and other inflammatory diseases. The present invention comprises the development of a group of sphingosine 1-phosphate receptor 2 (S1P$_2$) receptor derivatives that function as S1P$_2$ antagonists that are useful as anti-angiogenesis agents in cancer, atherosclerosis, and in other inflammatory disorders by blocking or inhibiting the signaling of the sphingosine 1-phosphate 2 receptor (S1P$_2$).

SUMMARY OF THE INVENTION

Figure 1:
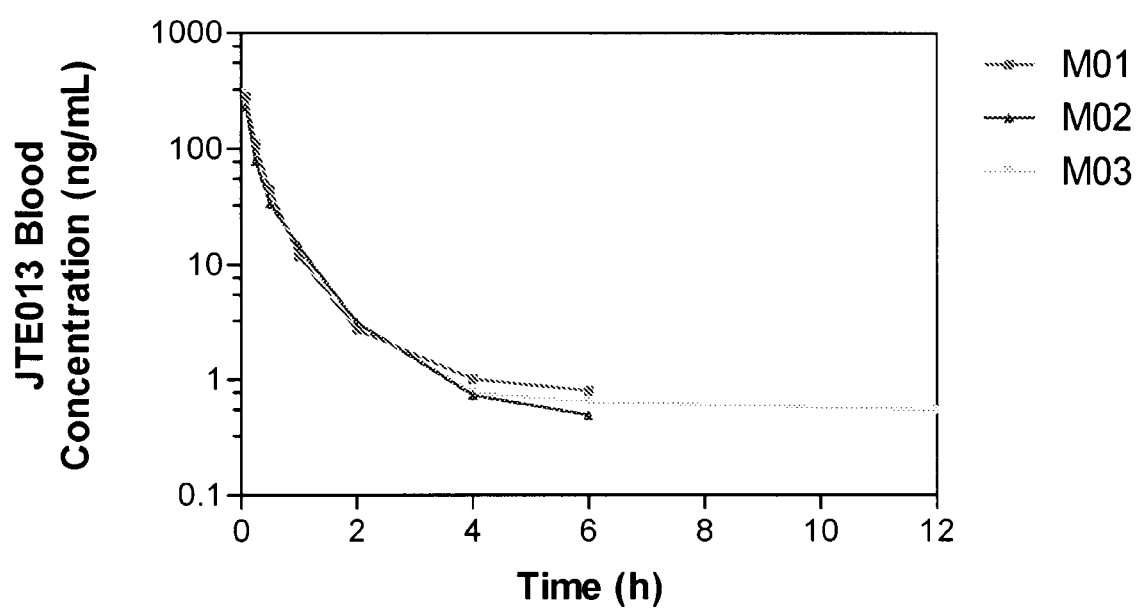
FIG. 1 is a graph illustrating JTE013 blood concentrations versus time following 1 mg/kg i.v. administration of JTE013 to group of 3 mice (M01-M03).
Figure 2:
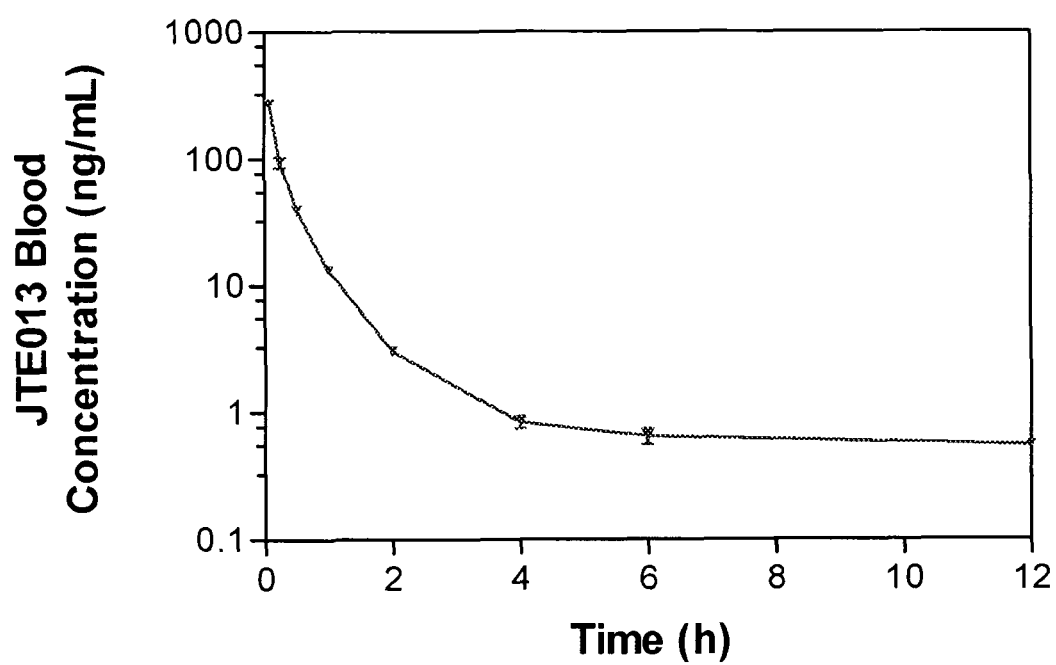
FIG. 2 is a graph illustrating mean (±S.D.) JTE013 blood concentrations following 1 mg/kg i.v. administration of JTE013 to group of 3 mice.
Figure 3:
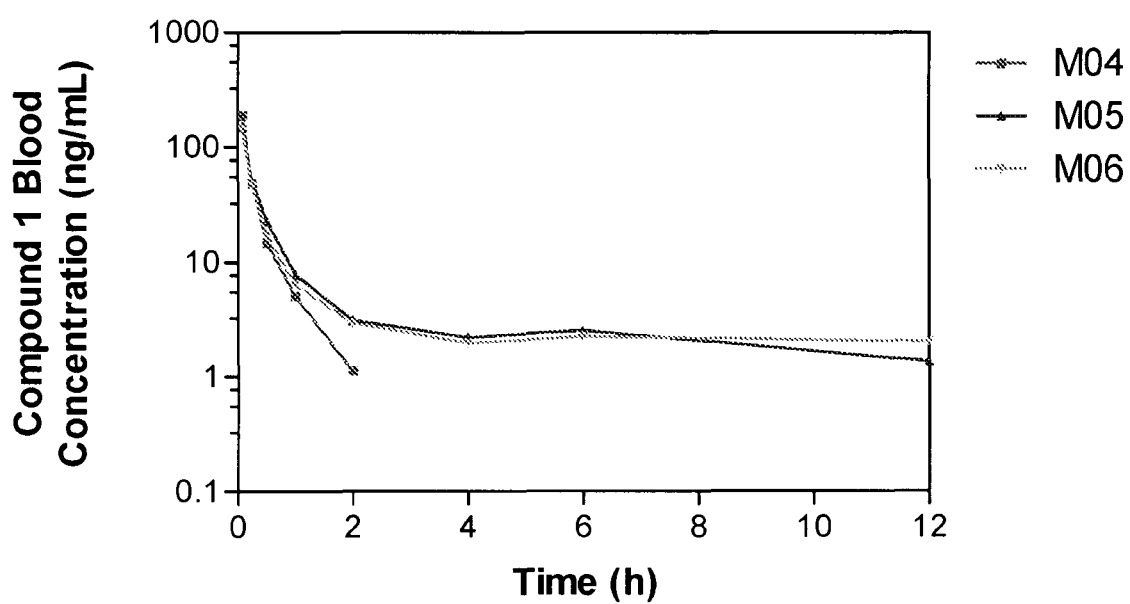
FIG. 3 is a graph illustrating Compound 1 blood concentrations versus time following 1 mg/kg i.v. administration of Compound 1 to group of 3 mice (M04-M06).
Figure 4:
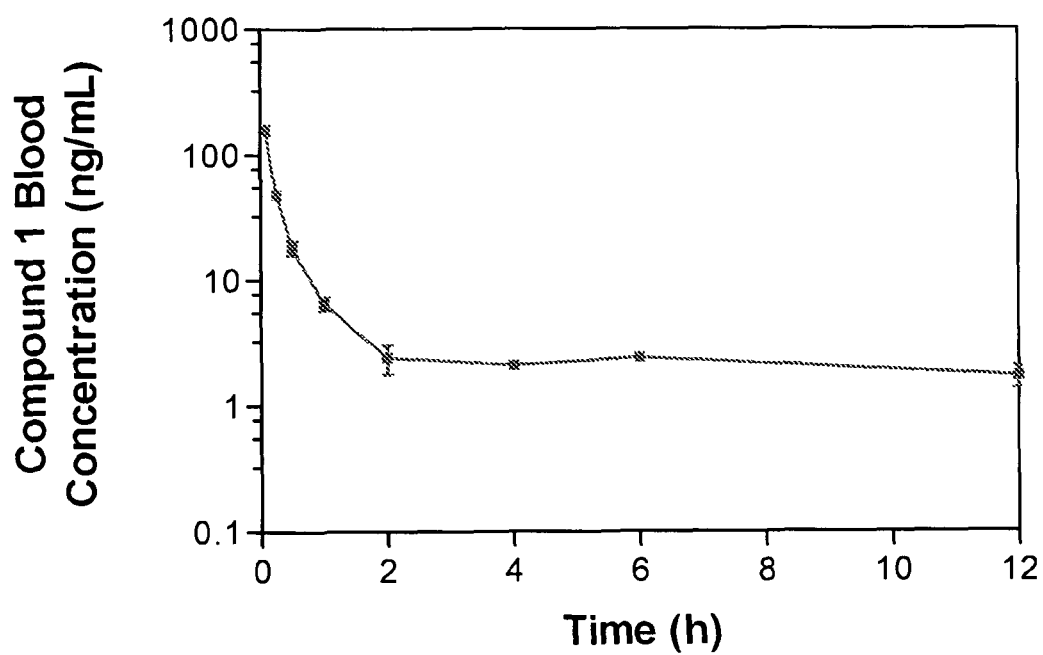
FIG. 4 is a graph illustrating mean (±S.D.) Compound 1 blood concentrations following 1 mg/kg i.v. administration of Compound 1 to group of 3 mice.
Figure 5:
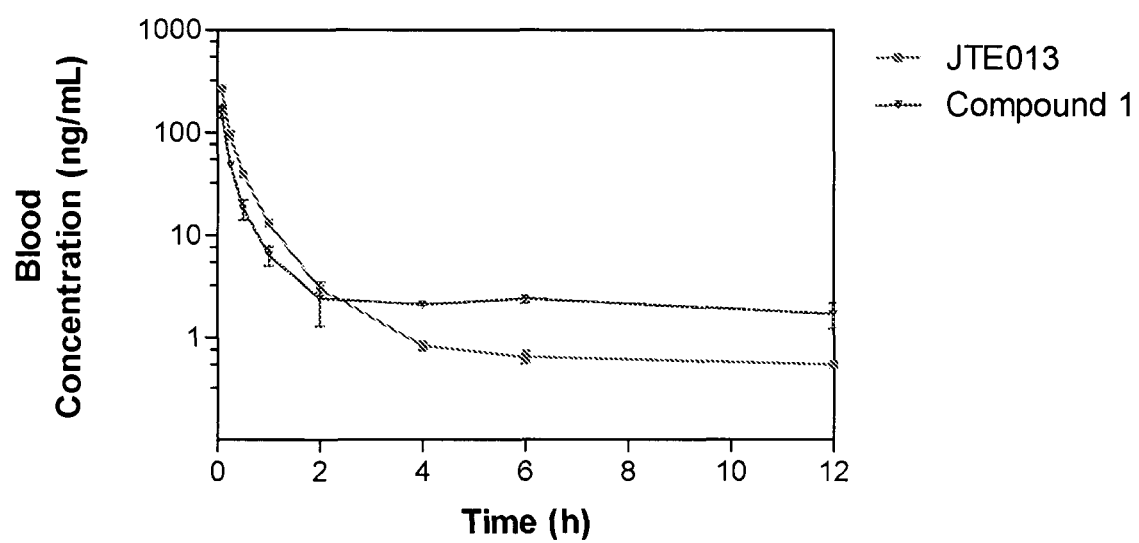
FIG. 5 is a graph illustrating mean (±S.D.) JTE013 and Compound 1 blood concentrations following 1 mg/kg i.v. administration to 2 groups of 3 mice.

The present invention comprises the development of a specific group of compounds that function as $S1P_2$ antagonists useful as anti-angiogenesis agents for the treatment of cancer, atherosclerosis, and in other inflammatory disorders by blocking or inhibiting a sphingosine 1-phosphate 2 receptor ($S1P_2$) The $S1P_2$ antagonists could be useful in the treatment of glioblastoma multiforme, neuroblastoma and other cancers. These compositions are effective in the inhibition of abnormal angiogenesis in the eye, particularly in the retina, based on improved in vivo characteristics such as improved pharmacokinetic parameters, increased blood concentration levels over time and greater receptor affinity, based at least in part, on its slower clearance. Also provided herein are methods for treating or preventing certain types of blindness through the administration of compositions comprising a $S1P_2$ receptor antagonist and an opthalamically-acceptable excipient.

DETAILED DESCRIPTION OF THE INVENTION

Pathological angiogenesis and several types of inflammatory disease have been correlated with increased $S1P_2$ receptor levels. In the prior art, JTE013 is a known selective $S1P_2$ receptor antagonist compound. This compound has very poor in vivo characteristics, based at least in part on its rapid clearance. These characteristics may limit the efficacy and usefulness of this compound in treating and preventing sphingosine-1-phosphate-mediated diseases.

The present invention then, comprises compositions and methods for the inhibition of abnormal angiogenesis in the eye, particularly in the retina. Also provided herein are methods for treating or preventing certain types of blindness. Further provided are compositions comprising a $S1P_2$ receptor antagonist and an opthalamically-acceptable excipient with improved in vivo characteristics. The present invention comprises compositions and methods for the inhibition of abnormal angiogenesis in the eye, particularly in the retina. Also provided herein are methods for treating or preventing certain types of blindness. Further provided are compositions comprising a $S1P_2$ receptor antagonist and an opthalamically-acceptable excipient, with improved in vivo characteristics, based on metabolic stability and/or increased duration of action.

Sphingosine-1-phosphate (S1P) is a multi-functional lipid mediator that signals via the S1P family of G protein-coupled receptors ($S1P_R$). S1P is known to regulate vascular maturation, permeability and angiogenesis. For example, S1P is known to be a stimulator of angiogenesis, i.e., new blood vessel growth. As used herein, the terms $S1P_{2R}$, $S1P_{2R}$, $S1P_2$ receptor and $S1P_2$ receptor are used interchangeably to mean the sphingosine-1-phosphate receptor 2.

A number of novel sphingosine 1-phosphate receptor 2 ($S1P_2$) antagonists were prepared. Details for making antagonist compounds are provided in the examples. These compounds showed unexpectedly enhanced stability to liver microsomes using a well-established in vitro model for in vivo metabolism and metabolic stability. In addition, most of these compounds unexpectedly bound to both $S1P_2$ and $S1P_5$ receptors. The compounds have utility as therapeutic drugs for the treatment and prevention of conditions or diseases mediated by S1P receptors. Such conditions and diseases include, but are not limited to a wide variety of inflammatory diseases and conditions as well as diseases and conditions mediated by angiogenesis processes.

In one embodiment of the present invention, the novel sphingosine-1-phosphate antagonist compounds may be used to treat or prevent atherosclerosis and conditions associated therewith, including cardiovascular and cerebral vascular diseases, such as, for example, myocardial infarction, stroke, angina and peripheral vascular disease. These compounds also may be used to treat or prevent sepsis and septic shock, as well as a wide variety of other diseases including diabetes, liver cirrhosis, vascular diseases with increased permeability, and allergic reactions. The general method of synthesis of these compounds is as follows:

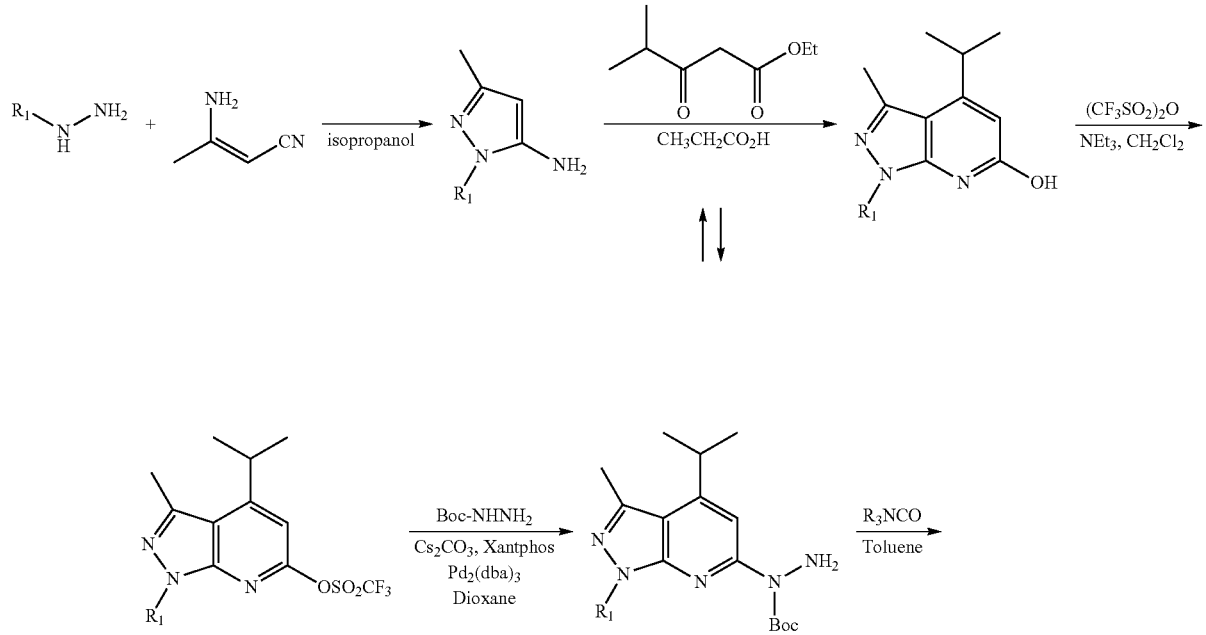

Scheme 1

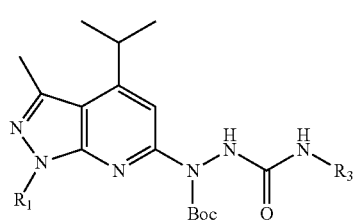
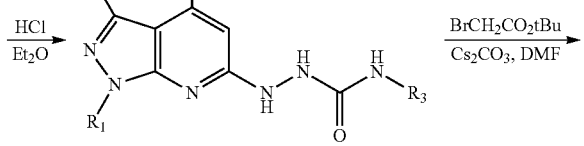

-continued

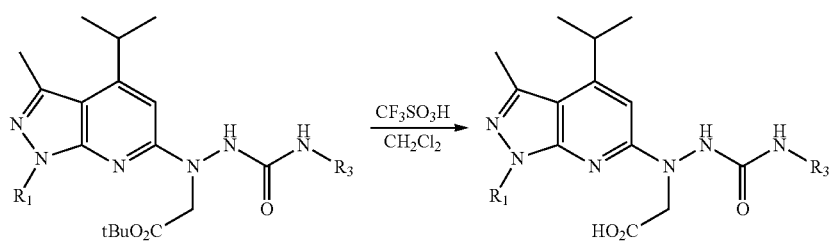

The preferred compounds of the present invention comprise those of the general structure

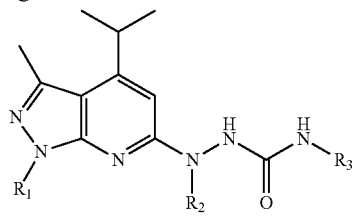

Wherein each consists of the following:

The following examples are provided to more specifically set forth and define the process of the present invention. It is recognized that changes may be made to the specific parameters and ranges disclosed herein and that there are a number of different ways known in the art to change the disclosed variables. And whereas it is understood that only the preferred embodiments of these elements are disclosed herein as set forth in the specification and drawings, the invention should not be so limited and should be construed in terms of the spirit and scope of the claims that follow herein.

| Compound No. | $R_1$ | $R_2$ | $R_3$ |
|---|---|---|---|
| 1. | -allyl | —H | 4-substituted-2,6-dichloropyridine |
| 2. | —CH$_3$ | —CH$_2$CO$_2$H | 4-substituted-2,6-dichloropyridine |
| 3. | -allyl | —CH$_2$CO$_2$H | 4-substituted-2,6-dichloropyridine |
| 4. | —CH$_3$ | -allyl | 4-substituted-2,6-dichloropyridine |
| 5. | | | |
| 6. | | | |

Wherein allyl is —CH$_2$CH=CH$_2$

Example 1 a. Synthesis of 5-amino-1-allyl-3-methylpyrazole

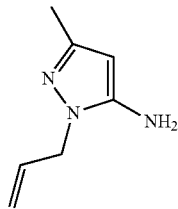

β-Amino-crotononitrile (4.2 g, 50 mmol) and allylhydrazine (3.6 g, 50 mmol) were dissolved in isopropanol (20 mL) and the solution was gradually heated to reflux under nitrogen atmosphere for 5 h. The reaction mixture was concentrated and purified by column chromatography using 2.5% methanol in DCM to give 5-methylpyrazole (4.2 g) as a syrup. $^1$H 300 MHz NMR (CDCl$_3$): δ 6.00-5.88 (1H, m), 5.35 (1H, s), 5.23-5.04 (2H, m), 4.56 (2H, dd, J=3.6 Hz, 1.5 Hz), 3.47 (2H, bs) 2.15 (3H, s).

b. Synthesis of 1H-6-hydroxy-4-isopropyl-1-allyl-3-methylpyrazolo[3,4-b]pyridine

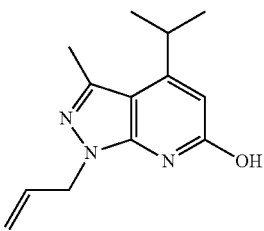 [SMILES: C=CCn1nc(C)c2c(C(C)C)cc(O)nc21]

Ethyl isobutyryl acetate (10.5 g, 66.5 mmol) was added to a solution of 5-amino-1-allyl-3-methylpyrazole (9.00 g, 65.7 mmol) in propionic acid and heated to reflux for 20 h. After cooling, ethyl acetate (80 mL) was added and heated to reflux for 1 h. The solvent was evaporated and the residue was purified by column chromatography using 5% methanol in DCM to give 1H-6-hydroxy-4-isopropyl-1-allyl-3-methylpyrazolo[3,4-b]pyridine as colorless crystals (1.1 g, 7%). $^1$H 300 MHz NMR (CDCl$_3$) δ 6.16 (1H, s), 6.06-5.97 (1H, m), 5.30-5.22 (2H, m), 4.95 (2H, dd, J=3.6 Hz, 1.5 Hz), 3.31-3.27 (1H, m), 2.52 (3H, s), 1.31 (6H, d, J=7 Hz).

Example 2

Synthesis of 2,6-dichloropyridyl-4-isocyanate

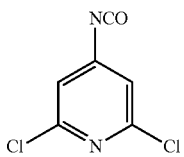

a) Synthesis of 2,6-dichloropyridine-4-carbonylazide

Diphenylphosphoryl azide (DPPA) (5 mL, 23.2 mmol) was added to a solution of 2,6-dichloroisonicotinic acid (4.05 g, 21 mmol) and tri-ethylamine (3.8 mL, 27.5 mmol) in ethyl acetate (40 mL) at 0-5° C., and stirred for 20 h at room temperature. Ethyl acetate was added for dilution and the organic layer was washed with water. The organic layer dried over Na$_2$SO$_4$, filtered and concentrated under vacuum to get crude product of 2,6-dichloropyridine-4-carbonylazide (7.08 g). It was dissolved in ethyl acetate and treated with activated carbon. After filtration and evaporation, 2,6-dichloropyridine-4-carbonylazide (4.57 g) was obtained as colorless crystals. The 2, 6-dichloropyridine-4-carbonylazide (4.21 g) that was obtained from the above procedure was dissolved into dry toluene (40 mL) and the solution was heated for 4 h at 100° C. to give 2,6-dichloropyridyl-4-isocyanate. It was stored as a solution at 0° C.

Synthesis of Compound 1

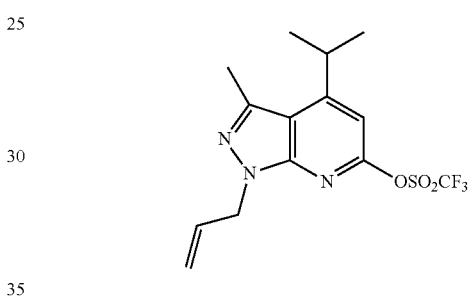

Tri-ethyl amine (2.17 mL, 3.0 eq, 15.57 mmol) was added to a solution of 1H-6-hydroxy-4-isopropyl-1-allyl-3-methylpyrazolo[3,4-b] pyridine (1.20 g, 5.19 mmol) in dichloromethane (30 mL) and cooled to −10° C. Trifluoromethanesulphonic anhydride (1.30 mL, 7.78 mmol, 1.5 eq) was added to this cold solution dropwise. The solution was stirred for 45 minutes or until completion by TLC monitoring. The reaction was quenched with water and extracted with dichloromethane (3×10 mL). The mixture was concentrated, dried and purified by column chromatography (10:1 Hexane/Ethyl Acetate) to give 1.32 g of the desired product as a yellow oil in 70% yield. $^1$H 300 MHz NMR (CDCl$_3$): δ 6.75 (1H, s), 6.06-5.95 (1H, m), 5.29-5.22 (2H, m), 4.95 (2H, dd, J=3.0 Hz, 1.5 Hz), 3.65-3.60 (1H, m), 2.69 (3H, s) and 1.38 (6H, d, J=6.6 Hz).

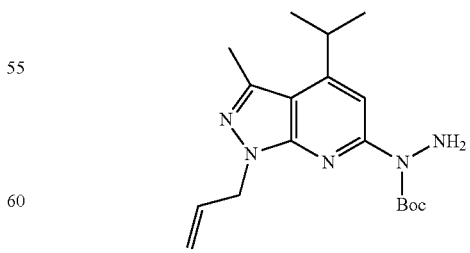

The compound above (200 mg, 0.551 mmol), t-butyl carbazate (87 mg, 0.661 mmol, 1.2 eq), oven dried cesium carbonate (431 mg, 1.322 mmol, 2.4 eq), Xantphos (15% mol, 48 mg, 0.082 mmol) and Pd$_2$(dba)$_3$ (5% mol, 26 mg, 0.0276 mmol) were all placed in an oven dried flask under nitrogen. This reaction mixture was dissolved in dry degassed dioxane and heated at 65° C. for 12 h or until completion by TLC monitoring. Material was concentrated and subjected to column chromatography (3:1 Hexanes/Ethyl Acetate) to give 133 mg of the desired hydrazine derivative in 70% yield $^1$H 300 MHz NMR (CDCl$_3$) δ 7.34 (1H, s), 6.01 (1H, m), 5.22 (1H, m), 5.16 (1H, m), 4.97 (2H, d, J=6 Hz), 4.34 (2H, bs), 3.59 (1H, m) 2.65 (3H, s), 1.55 (9H, s), 1.34 (3H, s) 1.36 (3H, s).

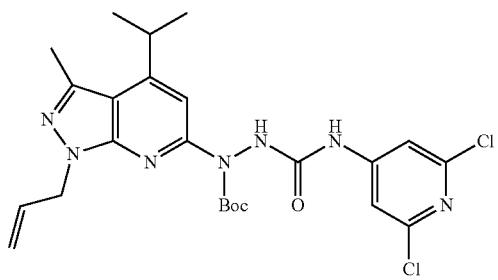 [SMILES: C=CCn1nc(C)c2c(C(C)C)cc(N(NC(=O)Nc3cc(Cl)nc(Cl)c3)C(=O)OC(C)(C)C)nc21]

A solution of 2,6-dichloro-pyridyl-4-isocyanate (2.0 eq, 1.3 mL, 0.771 mmol) in toluene was added to the above hydrazine derivative (133 mg, 0.385 mmol) in THF (5 mL) and stirred for 12 h or until completion by TLC monitoring. The crude reaction was concentrated, purified by column chromatography (2:1 to 1:1 Hexanes/Ethyl Acetate) to afford the desired product as a yellow solid. (193 mg, 94% yield). $^1$H 300 MHz NMR (CDCl$_3$) δ 9.56 (1H, bs), 7.44 (2H, s), 7.25 (1H, s), 7.10 (1H, bs) 6.10-5.97 (1H, m), 5.24 (1H, dd, J=7.5 Hz, 1.5 Hz), 5.01 (1H, dd, J=7.5 Hz, 1.5 Hz), 4.98-4.95 (2H, m), 3.69-3.60 (1H, m), 2.70 (3H, s), 1.55 (9H, s), 1.40 (6H, d, J=7 Hz).

Synthesis of Compound 1

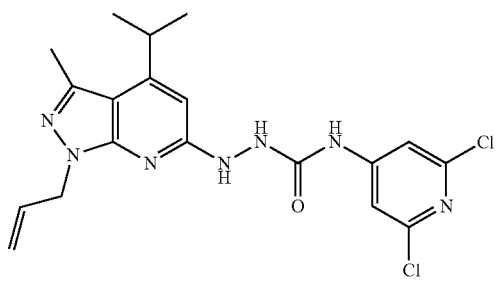 [SMILES: C=CCn1nc(C)c2c(C(C)C)cc(NNC(=O)Nc3cc(Cl)nc(Cl)c3)nc21]

Hydrochloric acid (2M in ether, 5 mL, 10 mmol) was added to a solution of the above Boc-compound (500 mg, 0.94 mmol) in diethyl ether (10 mL) at 0° C., the reaction was stirred for 12 h at room temperature. The reaction mixture concentrated, diluted with DCM (20 mL), washed with sat NaHCO3 solution (15 mL), dried and concentrated to afford crude product (424 mg). The pure product (Compound-1) was isolated after purification by using preparative TLC (30% EtOAc in hexanes) as a white solid (140 mg, yield 34%). $^1$H 300 MHz NMR (CDCl$_3$+CD$_3$OD) δ 7.41 (2H, s), 6.38 (1H, s (1H, m), 5.07-4.97 (2H, m), 4.77 (2H, d, J=6 Hz), 3.41-3.29 (1H, m), 2.51 (3H, s), 1.24 (6H, d, J=7 Hz), MS (m/z MH+) 434.2.

N-(1H-4-isopropyl-1,3-dimethylpyrazolo[3,4-b]pyridine-6-yl)amino-N'-(2,6-dichloropyridine-4-yl) urea (JTE013)

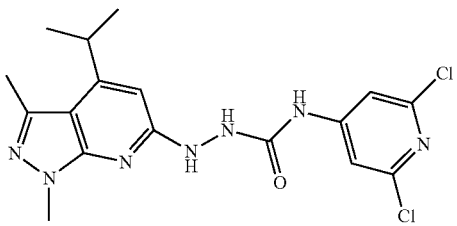 [SMILES: Cc1nn(C)c2nc(NNC(=O)Nc3cc(Cl)nc(Cl)c3)cc(C(C)C)c12]

The above titled compound was prepared as reported in literature (WO 01/98301)

Synthesis of Compound-2

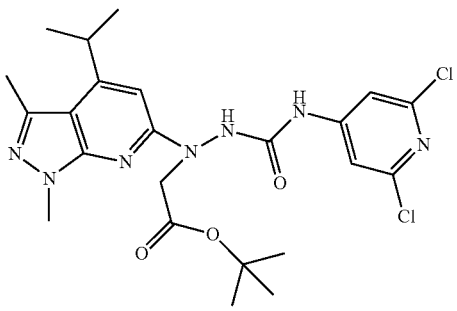 [SMILES: Cc1nn(C)c2nc(N(CC(=O)OC(C)(C)C)NC(=O)Nc3cc(Cl)nc(Cl)c3)cc(C(C)C)c12]

tert-Butyl bromoacetate (500 mg, 2.60 mmol) was added to a solution of N-(1H-4-isopropyl-1, 3-dimethylpyrazolo[3,4-b]pyridine-6-yl)amino-N'-(2,6-dichloropyridine-4-yl) urea (125 mg, 0.306 mmol) in dry DME (1 mL) and the reaction mixture heated overnight at 100° C. It was then diluted with DCM (20 mL) and washed with aqueous NaHCO$_3$ (1×10 mL) followed by water (2×10 mL). The organic layer was dried over Na$_2$SO$_4$, and concentrated under reduced pressure. The residue was purified by column chromatography (5% MeOH/CH$_2$Cl$_2$) to give the desired pure product as a white solid (25 mg). $^1$H 300 MHz NMR (CD$_3$OD) δ 7.58 (2H, s), 6.78 (1H, s), 4.87 (2H, bs), 3.99 (3H, s), 3.65 (1H, m), 2.81 (3H, s), 1.50 (9H, s), 1.37 (6H, d, J=6.6 Hz), MS (m/e) 523 (MH+).

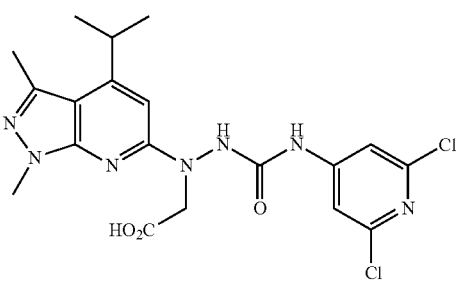 [SMILES: Cc1nn(C)c2nc(N(CC(=O)O)NC(=O)Nc3cc(Cl)nc(Cl)c3)cc(C(C)C)c12]

The above t-butyl ester (15 mg, 0.028 mmol) dissolved in DCM (1 mL) was added to a solution of trifluoromethanesulfonic acid (15 mg, 0.10 mmol) in dry DCM (3 mL) at 0° C. The reaction mixture was stirred for 1 h at room temperature. After completion of the reaction, as indicated by TLC, NaHCO₃ (9 mg) and MeOH (0.5 mL) were added to the reaction mixture and stirred for 15 min. The reaction mixture was concentrated under vacuum, co-evaporated with DCM and triturated with hexanes to get the desired product (Compound-2) as a brown colored solid (25 mg, contains 34% compound and 66% sodium triflate). $^1$H 300 MHz NMR (CD₃OD) δ 7.58 (2H, s), 6.78 (1H, s), 5.49 (2H, d, J=7.5 Hz), 4.00 (3H, s), 3.44-3.57 (1H, m), 2.82 (3H, s), 1.37 (6H, d, J=6.6 Hz), MS (m/z MH+) 466.2.

Synthesis of Compound-3

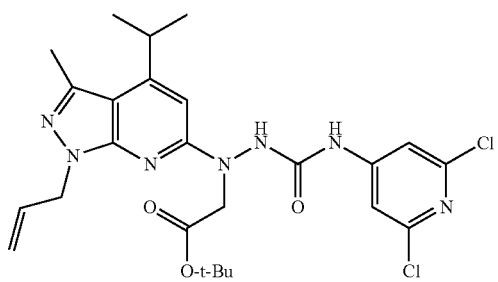

Cesium carbonate (140 mg, 0.4 mmol) was added to a solution of compound 1 (180 mg, 0.328 mmol) and tert-butyl bromoacetate (80 mg, 0.41 mmol) in dry DMF (1 mL). The reaction mixture stirred for 3 h at room temperature. It was then diluted with DCM (20 mL), washed with water (3×10 mL), dried over Na₂SO₄, and concentrated under reduced pressure. The desired product was isolated after purification using prep TLC (25% EtOAc/Hexanes) followed by trituration with isopropyl ether as colorless crystals (45 mg). $^1$H 300 MHz NMR (CDCl₃): δ 8.49 (1H, bs), 7.49 (2H, s), 7.01 (1H, bs), 6.40 (1H, s), 6.02-5.96 (1H, m), 5.21-5.15 (2H, m), 4.97 (1H, d, J=18 Hz), 4.96-4.88 (2H, m), 3.67 (1H, d, J=18 Hz), 3.55-3.42 (1H, m), 2.62 (3H, s), 1.47 (9H, s), 1.32 (6H, d, J=7 Hz), MS (m/z MH+) 447.

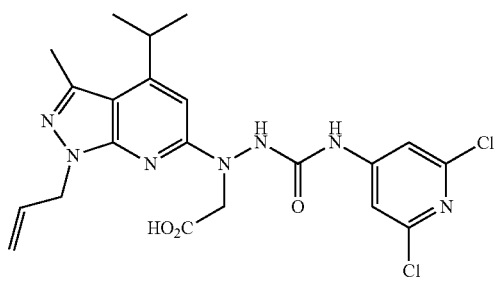 [SMILES: C=CCn1nc(C)c2c(C(C)C)cc(N(CC(=O)O)NC(=O)Nc3cc(Cl)nc(Cl)c3)nc21]

The Boc-protected compound above (22 mg, 0.04 mmol) dissolved in DCM (1 mL) was added to Trifluoromethane sulfonic acid (22 mg, 0.14 mmol) in dry DCM (4 mL) at 0° C. The reaction mixture was stirred for 1 h at room temperature. After completion of the reaction, as indicated by TLC, NaHCO₃ (11 mg) and MeOH (0.5 mL) were added to the reaction mixture and stirred for 15 min. Reaction mixture was concentrated under vacuum, co-evaporated with DCM and triturated with hexanes to get the desired product (Compound-3) as a light brown colored solid (36 mg, contains 34% compound and 66% sodium triflate). $^1$H 300 MHz NMR (CD₃OD) δ 9.69 (1H, bs), 7.67 (2H, s), 6.64 (1H, s), 5.97-5.91 (1H, m), 5.09-4.85 (6H, m), 3.57-3.34 (1H, m), 2.60 (3H, s), 1.36 (6H, d, J=7 Hz), MS (m/e MH+) 490.

Synthesis of Compound 4

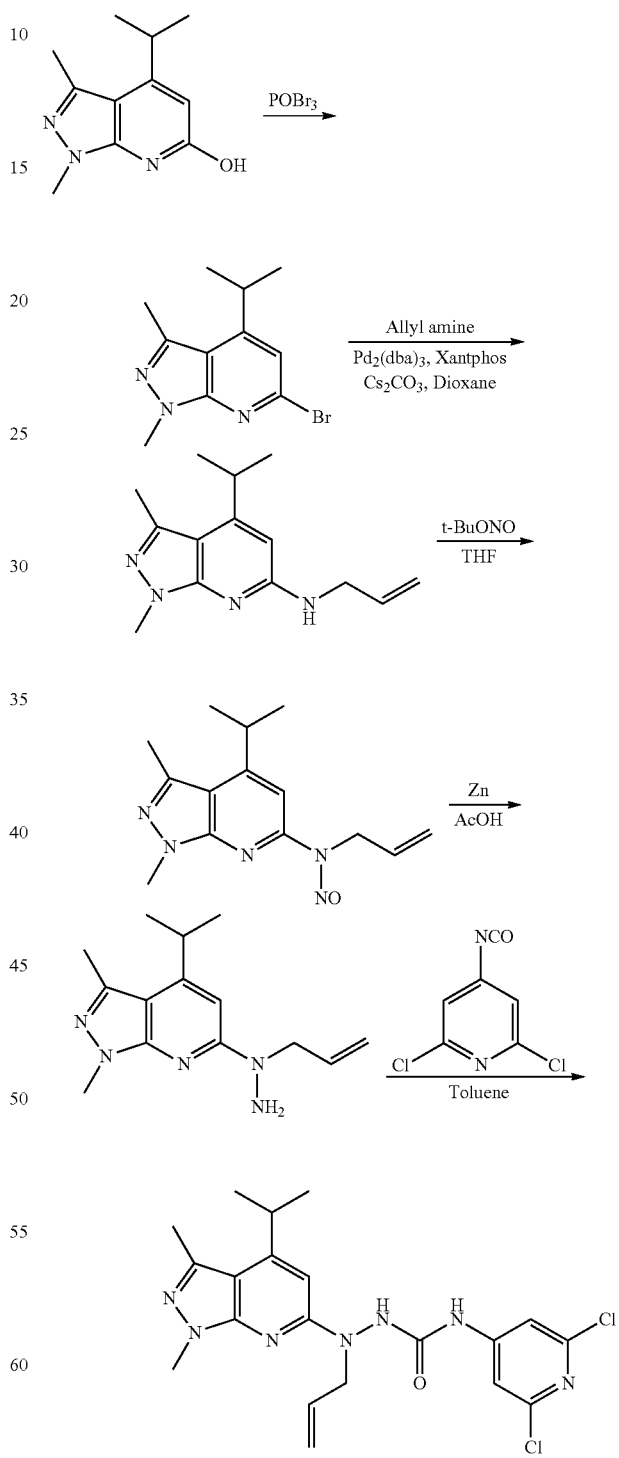

Compound 4 was prepared as in the scheme above. MS (m/e MH+) 447.

Synthesis of Compound-5

Synthesis of 1H-6-hydroxy-4-trifluoromethyl-1-allyl-3-methylpyrazolo[3,4-b] pyridine

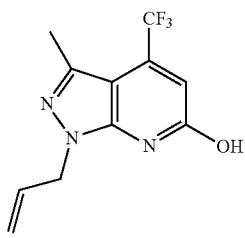 [SMILES: C=CCn1nc(C)c2c(C(F)(F)F)cc(O)nc21]

Ethyl-4,4,4-trifluoroacetoacetate (5.6 g, 30 mmol) in propionic acid (10 mL) was added to a solution of 5-amino-1-allyl-3-methylpyrazole (4.2 g, 30 mmol) in propionic acid and heated (150° C.) to reflux for 23 h. After cooling, ethyl acetate (40 mL) was added and heated to reflux for 1 h. On slow cooling, crystals of the desired compound were deposited, which were filtered, washed ethyl acetate and dried under reduced pressure. Thus 1H-6-hydroxy-4-trifluoromethyl-1-allyl-3-methylpyrazolo[3,4-b] pyridine (5.1 gm, 66%) was obtained as white crystals, $^1$H 300 MHz NMR (CDCl$_3$) δ 6.63 (1H, s), 6.07-5.94 (1H, m), 5.29-5.23 (2H, m), 4.96 (2H, dd, J=3.0 Hz, 1.5 Hz), 2.51 (3H, s) and 1.85 (1H, bs).

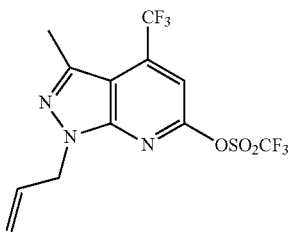

Tri-ethyl amine (1.77 g, 2.42 mL, 3.0 eq, 17.52 mmol) was added to a solution of 1H-6-hydroxy-4-trifluoromethyl-1-allyl-3-methylpyrazolo[3,4-b] pyridine (1.50 g, 5.84 mmol) in dichloromethane (30 mL) and cooled to −10° C. Trifluoromethanesulfonic anhydride (1.48 mL, 2.47 g, 8.75 mmol, 3.0 eq) was added to this cold solution. The solution was stirred at this temperature for 45 minutes or until completion by TLC monitoring. The reaction was quenched with water and extracted with dichloromethane (3×10 mL). The organic layer was concentrated, dried and purified by column chromatography (10:1 Hexane/Ethyl Acetate) to give 2.15 g of the desired product as yellow oil. 96% yield $^1$H 600 MHz NMR (CDCl$_3$) δ 6.60 (1H, s), 6.03 (1H, m), 5.30 (2H, m), 4.98 (2H, dd, J=6.0 Hz, 1.5 Hz), 2.49 (3H, s).

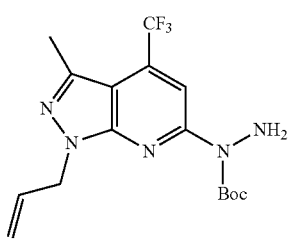 [SMILES: C=CCn1nc(C)c2c(C(F)(F)F)cc(N(N)C(=O)OC(C)(C)C)nc21]

The above compound (215 mg, 0.553 mmol), t-butyl carbazate (88 mg, 0.664 mmol, 1.2 eq), oven dried cesium carbonate (432 mg, 1.327 mmol, 2.4 eq), Xantphos (15% mol, 48 mg, 0.083 mmol) and Pd$_2$(dba)$_3$ (5% mol, 25 mg, 0.0276 mmol) were all placed in a flask dry under a nitrogen atmosphere. This reaction mixture was dissolved in dry degassed dioxane and heated at 65° C. for 12 h or until completion by TLC monitoring. The reaction mixture was concentrated and the material was subjected directly to column chromatography (3:1 Hexanes/Ethyl Acetate) to give 85 mg of the desired product in 42% yield $^1$H 300 MHz NMR (CDCl$_3$) δ 7.93 (1H, s), 6.04 (1H, m), 5.24 (2H, m), 5.02 (2H, dd, J=6.0 Hz, 1.5 Hz), 4.91 (2H, bs) 2.59 (3H, s), 1.58 (9H, s).

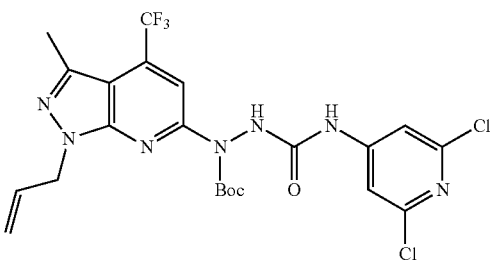 [SMILES: C=CCn1nc(C)c2c(C(F)(F)F)cc(N(NC(=O)Nc3cc(Cl)nc(Cl)c3)C(=O)OC(C)(C)C)nc21]

A solution of 2,6-dichloro-pyridyl-4-isocyanate (~2.0 eq, 1.0 mL, 0.458 mmol) in toluene was added to a solution of the above hydrazine derivative (85 mg, 0.229 mmol) in THF (5 mL) at 0-5° C. The solution was stirred for 12 h or until completion by TLC monitoring. The reaction was concentrated and directly purified by column chromatography (2:1 to 1:1 Hexanes/Ethyl Acetate) to afford 122 mg of the desired Boc product in 95% yield $^1$H 600 MHz NMR (CDCl$_3$) δ 8.75 (1H, bs), 8.06 (1H, bs), 7.72 (1H, s), 7.32 (2H, s), 6.01 (1H, m), 5.24 (2H, d J=5.6 Hz, 2.5 Hz), 5.00 (2H, d, J=5.4 Hz), 2.64 (3H, s), 1.57 (9H, s). 5.

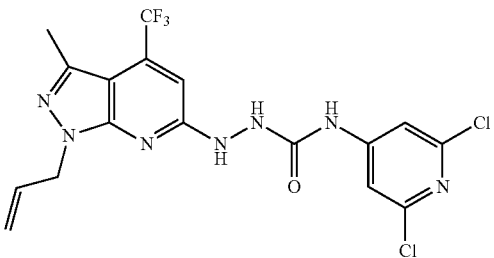 [SMILES: C=CCn1nc(C)c2c(C(F)(F)F)cc(NNC(=O)Nc3cc(Cl)nc(Cl)c3)nc21]

Hydrochloric acid (2M sol in ether, 1.0 mL, 2 mmol) was added to a solution of the above Boc derivative (44 mg, 0.095 mmol) in dry dichloromethane (5 mL) at 0° C. The reaction mixture was stirred for 12 h at room temperature. The reaction mixture was filtered and the crystalline compound thus obtained was washed with isopropyl ether and dried in a vacuum oven. Compound-5 was isolated as a colorless solid (26 mg, yield 72%). $^1$H 300 MHz NMR (CD$_3$OD) δ 7.60 (2H, s), 6.93 (1H, s), 5.97-5.88 (1H, m), 5.08-4.92 (2H, m), 4.91-4.88 (2H, m), 2.49 (3H, s), MS (m/e MH+) 460.

Synthesis of Compound-6

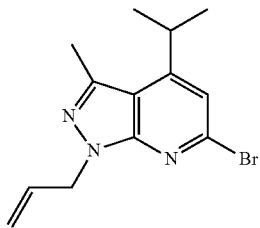 [SMILES: C=CCn1nc(C)c2c(C(C)C)cc(Br)nc21]

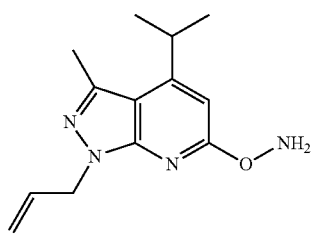

POBr₃ (365 mg, 1.29 mmol) was added to a solution of 1H-6-hydroxy-4-isopropyl-1-allyl-3-methylpyrazolo[3,4-b]pyridine (200 mg, 0.86 mmol) in anisole (1 mL). The reaction mixture was heated for 3 h at 130° C. After completion of reaction as indicated by TLC, reaction mixture diluted with toluene (10 mL). It was washed with saturated NaHCO₃ (10 mL) followed by saturated aqueous NaCl (10 mL), dried over Na₂SO₄ and filtered. The filtrate was evaporated under reduced pressure and the resulting residue was purified by column chromatography using 10% ethyl acetate/hexanes as eluent. The desired product (compound 6) was obtained as yellow oil (108 mg, Yield: 42%). ¹H 300 MHz NMR (CDCl₃) δ 7.03 (1H, s), 6.15 (1H, m), 5.22-5.16 (2H, m), 5.02 (2H, dd, J=6.0 Hz, 1.5 Hz), 3.62-3.45 (1H, m), 2.62 (3H, s), 1.38 (6H, d, J=6.0 Hz).

Sulfuric acid (0.01 mL) was added to a solution of above acetohydroxamate compound (80 mg, 0.25 mmol) in methanol (4 mL). The reaction mixture was stirred for 2.5 h at room temperature. After completion of the reaction as indicated by TLC, it was neutralized with Na₂CO₃ (108 mg), added water (10 mL) and extracted with EtOAc (3×10 mL). The organic layers were combined, dried over Na₂SO₄ and evaporated under reduced pressure. The crude amine (60 mg, Yield: 96%) used for next reaction without further purification. ¹H 300 MHz NMR (CDCl₃) δ 6.55 (2H, bs), 6.49 (1H, s), 6.08-5.97 (1H, m), 5.23-5.16 (2H, m), 4.96 (2H, dd, J=6.0 Hz, 1.5 Hz), 3.52-3.47 (1H, m), 2.62 (3H, s), 1.33 (6H, d, J=7.0 Hz).

Synthesis of Compound 6

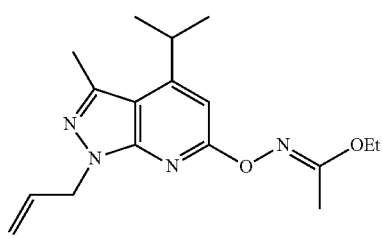 [SMILES: C=CCn1nc(C)c2c(C(C)C)cc(O/N=C(\C)OCC)nc21]

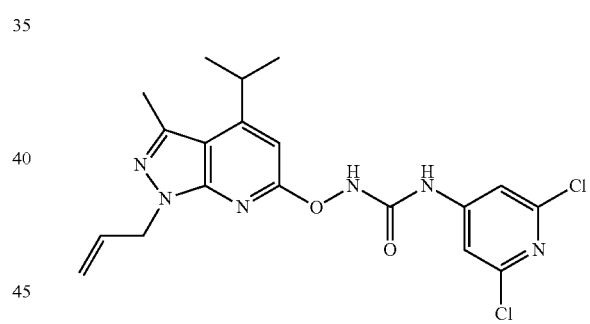

Potassium-tert-butoxide (1M solution, 1 mL) was added to a solution of ethyl-N-hydroxyacetimidate (105 mg, 102 mmol) in dry DMF (1 mL) at 0° C., and stirred for 2.5 h. The above bromo compound (100 mg, 0.34 mmol) dissolved in DMF (1 mL) at 0° C. was carefully added and stirring continued for 12 h at room temperature. The reaction mixture was quenched with water (5 mL) and extracted with ethyl acetate. The organic layer was dried over Na₂SO₄ and the solvent was removed under reduced pressure. The residue was purified by column chromatography (20% EtOAc/Hexanes) to give acetohydroxamate derivative as colorless oil (80 mg, Yield: 74%). ¹H 300 MHz NMR (CDCl₃) δ 6.91 (1H, s), 5.99 (1H, m), 5.23-5.17 (2H, m), 4.97 (2H, dd, J=6.0 Hz, 1.5 Hz), 4.28 (2H, q), 3.56 (1H, m), 2.63 (3H, s), 2.19 (3H, s), 1.39-1.33 (9H, m).

A solution of 2,6-dichloro-pyridyl-4-isocyanate (~2.0 eq, 1.1 mL, 0.48 mmol) in toluene was added to the above crude amine above (60 mg, 0.24 mmol) in dry THF (4 mL) at 0° C. The solution was stirred for 12 h or until completion by TLC monitoring. The solvent was removed under reduced pressure and the desired compound. 6 was isolated by column chromatography (EtOAc/Hexane) as a white solid (70 mg, Yield: 66%). ¹H 300 MHz NMR (CDCl₃) δ 8.67 (1H, s), 7.72 (1H, s), 7.48 (2H, s), 6.63 (1H, s), 5.99-5.94 (1H, m), 5.21-5.13 (2H, m), 4.94 (2H, dd, J=5.0 Hz, 1.5 Hz), 3.60-3.56 (1H, m), 2.65 (3H, s), 1.38 (6H, d, J=7 Hz), MS (m/e MH+) 435.

Using the above methods the following compounds can also be prepared The methods of synthesis for compounds 9 is shown below.

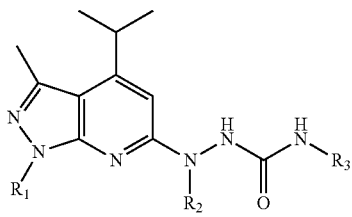

| Compound: | R₁ | R₂ | R₃ |
|---|---|---|---|
| No. 7 | —CH₃ | —CH₂CO₂Et | 4-substituted-2,6-dichloropyridine |
| No. 8 | —CH₃ | —CH₂CONH₂ | 4-substituted-2,6-dichloropyridine |
| No. 9 | —CH₃ | —CH₂CH₂OH | 4-substituted-2,6-dichloropyridine |
| No. 10 | —CH₃ | —CH₂SO₃H | 4-substituted-2,6-dichloropyridine |
| No. 11 | —CH₃ | —CH₂SO₂NH₂ | 4-substituted-2,6-dichloropyridine |
| No. 12 | —CH₃ | —CH₂PO₃H₂ | 4-substituted-2,6-dichloropyridine |
| No. 13 | —CH₂—CH=CF₂ | —H | 4-substituted-2,6-dichloropyridine |
| No. 14 | —CH₂CF=CH₂ | —H | 4-substituted-2,6-dichloropyridine |
| No. 15 | (E) —CH₂—CH=CFH | —H | 4-substituted-2,6-dichloropyridine |
| No. 16 | (Z) —CH₂CH=CFH | —H | 4-substituted-2,6-dichloropyridine |
| No. 17 | —CH₂-cyclopropyl | —H | 4-substituted-2,6-dichloropyridine |
| No. 18 | -cyclopropyl | —H | 4-substituted-2,6-dichloropyridine |
| No. 19 | -allyl | —H | 4-substituted-3,5-bis-trifluoromethylphenyl |
| No. 20 | —CH₃ | —CH₂CO₂H | 1-substituted-3,5-bis-trifluoromethylphenyl |
| No. 21 | -allyl | —H | 1-substituted-2,4-bis-trifluoromethylphenyl |
| No. 22 | —Me | —CH₂CO₂H | 1-substituted-2,4-bis-trifluoromethylphenyl |
| No. 23 | -allyl | —H | 3-substituted-5-trifluoromethyl-2-pyridone |
| No. 24 | —Me | —CH₂CO₂H | 3-substituted-5-trifluoromethyl-2-pyridone |
| No. 25 | -allyl | —H | 1-substituted-3,5-dichlorophenyl |
| No. 26 | —Me | —CH₂CO₂H | 1-substituted-3,5-dichlorophenyl |

N-(2,6-Dichloropyridin-4-yl)-2-(2-hydroxyethyl)-2-(4-isopropyl-1,3-dimethyl-1H-pyrazolo[3,4-b]pyridin-6-yl)hydrazine-1-carboxamide (compound 9)

2-(1-(4-Isopropyl-1,3-dimethyl-1H-pyrazolo[3,4-b]pyridin-6-yl)hydrazinyl)ethan-1-ol

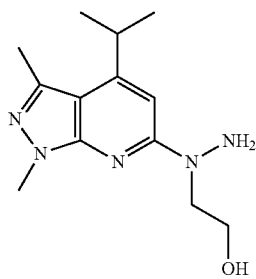 [SMILES: Cc1nn(C)c2nc(N(N)CCO)cc(C(C)C)c12]

2-Hydrazinoethanol (5.1 mL, 149.25 mmol) was added to a solution of 1H-6-bromo-4-isopropyl-1,3-dimethylpyrazolo[3,4-b]pyridine (2.0 g, 7.46 mmol) in ethanol (10 mL), and heated under reflux overnight. After cooling, it was stirred for four hours in an ice bath. The crude material was filtered and the obtained solid was triturated with a 50% aqueous ethanol (5 mL), filtered and dried under reduced pressure at 60° C. to give 2-(1-(4-Isopropyl-1,3-dimethyl-1H-pyrazolo[3,4-b]pyridin-6-yl)hydrazinyl)ethan-1-ol as white solid, 1.3 g (4.94 mmol, 66% yield). ¹H NMR (300 MHz, CDCl₃) δ 6.76 (s, 1H), 4.92 (brs, 2H), 4.20-3.96 (m, 2H), 3.94-3.86 (m, 2H), 3.84 (s, 3H), 3.52-3.45 (m, 2H), 2.58 (s, 3H), 1.25 (d, 6H, J=6.6 Hz).

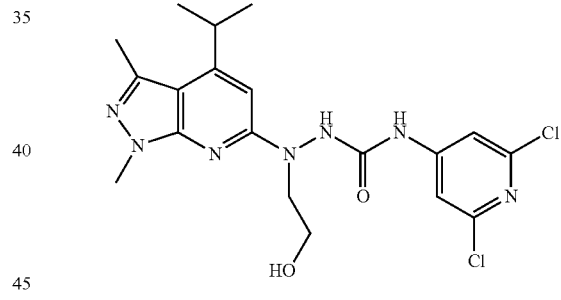

2,6-Dichloropyridine-4-carbonylazide (1.0 g, 4.61 mmol) was dissolved in toluene (10 mL) and the solution was stirred for 4 h at 100° C. After cooling to 0-5° C., a solution of 2-(1-(4-Isopropyl-1,3-dimethyl-1H-pyrazolo[3,4-b]pyridin-6-yl)hydrazinyl)ethan-1-ol (750 mg, 2.85 mmol) in THF (10 mL) was added and stirred for 18 hours at rt. After concentrating, the crude material was purified by column chromatography using gradient elution (0-20% methanol/DCM) to give N-(2,6-dichloropyridin-4-yl)-2-(2-hydroxyethyl)-2-(4-isopropyl-1,3-dimethyl-1H-pyrazolo[3,4-b]pyridin-6-yl)hydrazine-1-carboxamide as a white solid, 624 mg (1.38 mmol, 30% yield). ¹H NMR (300 MHz, CDCl₃) δ 9.28 (brs, 1H), 7.47 (s, 2H), 6.70 (brs, 1H), 6.58 (s, 1H), 4.70-4.50 (m, 1H), 4.30-4.20 (m, 1H), 4.08-3.98 (m, 1H), 3.91 (s, 3H), 3.53-3.46 (m, 2H), 2.92-2.70 (m, 1H), 2.60 (s, 3H), 1.32 (d, 6H, J=6.6 Hz). HRMS (ESI): mass calculated for $C_{19}H_{23}Cl_2N_7O_2$ [M+H]⁺, 452.1290 found, 452.1480.

Compounds 27-33 can be prepared as set forth and disclosed in published patent application WO2011041287A1 which is hereby incorporated by reference. The synthesis of compounds 27 and 33 are described below. These comprise the structure

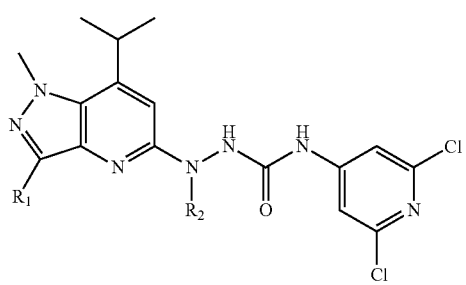
And consist of:
| Compound | R1 | R2 |
| --- | --- | --- |
| No. 27 | -allyl | H |
| No. 28 | —CH$_3$ | —CH$_2$CO$_2$H |
| No. 29 | —CH3 | —CH$_2$CONH$_2$ |
| No. 30 | —CH3 | —CH$_2$CH$_2$OH |
| No. 31 | —CH$_2$CF=CH$_2$ | H |
| No. 32 | —CH$_2$CH=CF$_2$ | H |
| No. 33 | —CH$_2$CH$_2$CH$_2$OH | H |
Synthesis of Compounds 27 and 33
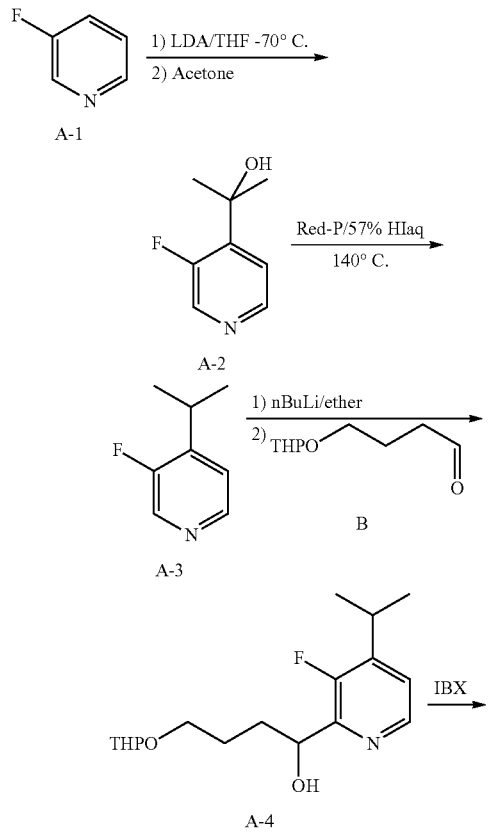
-continued
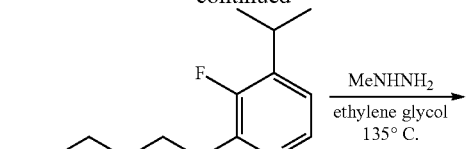
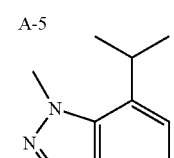
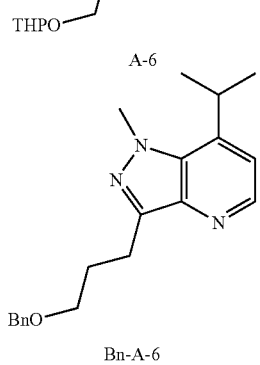
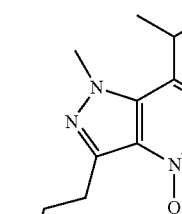
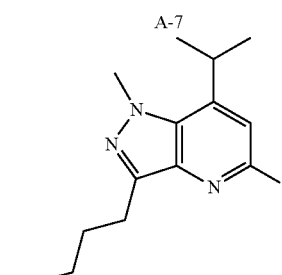
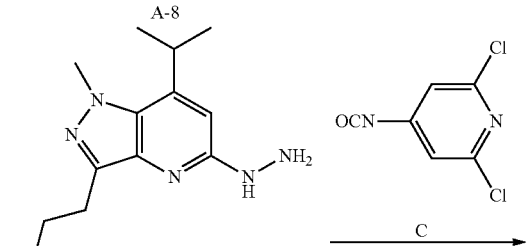

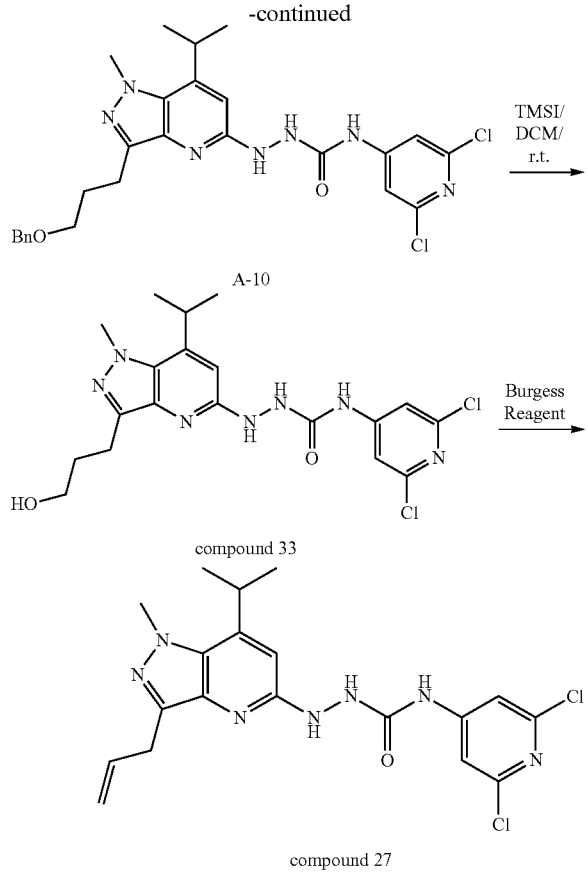

with ethyl aceate. The organic layer was washed with brine, dried with anhydride $Na_2SO_4$ and concentrated. The compound was purified by flash chromatography (petroleum ether:ethyl acetate=20:1~10:1) and gave compound A-5 (6 g, yield 60%).

Preparation of Compound A-6

MeNHNH$_2$ (10 mL) was added to a solution of compound A-5 (6 g, 19.4 mmol) in glycol (3 mL). The solution was heated to reflux at 140° C. overnight. Water (50 ml) was added and the solution was extracted with dichloromethane. The organic layer was washed with brine, dried with anhydride $Na_2SO_4$, concentrated, and purified by flash chromatography to give compound A-6 (3 g, yield 50%).

Preparation of Compound Bn-A-6

6M HCl (10 mL) was added to a solution of compound A-6 (3 g, 9.5 mmol) in THF (50 mL). The reaction was stirred at RT for 1 h, quenched with $NaHCO_3$(aq.), extracted with ethyl acetate. The organic layer was washed with brine, dried with anhydride $Na_2SO_4$ and concentrated to give comp A-6-1. NaH (760 mg, 19 mmol) was added to compound A-6-1 in THF (50 mL), the solution was stirred at 60° C. for 2 h. The solution was cooled to 0° C. and BnBr (3.23 g, 19 mmol). The solution was warmed to RT and stirred overnight. Water (20 mL) was added, and the solution extracted with ethyl acetate. The organic layer was washed with brine, dried with anhydride $Na_2SO_4$ and concentrated to give compound Bn-A-6 (2.7 g, yield 90%).

Preparation of Compound A-7 m-Chloroperbenzoic acid (MCPBA, 3.7 g, 16.7 mmol) was added to a solution of compound Bn-A-6 (2.7 g, 8.4 mmol) in CHCl$_3$ (30 mL) at 0° C. The solution was heated to reflux at 90° C. for 3 h. The solution was quenched with $NaHCO_3$(aq.) and extracted with DCM. The organic layer was washed by brine, dried with anhydride $Na_2SO_4$ and concentrated to give crude compound A-7 (3 g)

Preparation of Compound A-8

POCl$_3$ (5 mL) was added to a solution of compound A-7 (3 g, 8.8 mmol) in toluene (30 mL). The the solution was stirred at 90° C. for 3 h, then concentrated and quenched with $NaHCO_3$ (aq.), extracted with ethyl acetate. The organic layer was washed by brine, dried with anhydride $Na_2SO_4$ and concentrated to give compound A-8 (800 mg, yield 25%).

Preparation of Compound A-9

To a solution of compound A-8 (250 mg, 0.7 mmol), and $NH_2NH_2$ (aq) in EtOH (1 ml) was stirred at 120° C. for 12 h in a CEM Microwave. The solution was cooled and extracted with ethyl acetate. The organic layer was washed by brine, dried with anhydride $Na_2SO_4$ and concentrated to give crude compound A-9 (200 mg).

Preparation of Compound A-10

2,6-Dichloro-4-isocyanate pyridine (compound C, 160 mg, 0.85 mmol) was added to a solution of compound A-9 (200 mg, 0.56 mmol) in THF (5 mL). The solution was stirred at RT for 30 min. Methanol was added and the resulting solid was filtered. The filtrate was concentrated and compound A-10 was purified by preparative TLC (100 mg, yield 33%).

Preparation of Compound 33

Trimethyl silyl iodide (0.5 mL) was slowly added to a solution of A-10 (100 mg, 0.18 mmol) in dichloromethane. The solution was stirred at RT for 30 min, quenched with $NaHCO_3$ (aq), and extracted with DCM. The organic layer was washed by brine, dried with anhydride $Na_2SO_4$ and concentrated to give compound 33 (40 mg, yield 48%).

$^1$HNMR (400 MHz, CDCl3) δ: 8.68 (1H, br), 7.55 (1H, br), 7.40 (2H, s), 7.00 (1H, s), 6.71 (1H, s), 4.18 (3H, s),

Preparation of Compound A-2

LDA (247 mL, 1 M) was slowly added to a solution of compound A-1 (20 g, 206 mmol) in THF (300 mL) at −78° C. The solution was stirred at −78° C. for 1 h, then acetone (100 mL) was added. The reaction was stirred for 1 h, then quenched with $NH_4Cl$ (aq.) and extracted with ethyl acetate. The organic layer was washed by brine, dried with anhydride $Na_2SO_4$ and concentrated to give crude compound A-2.

Preparation of Compound A-3

Red-P (20 g), was added to a solution of compound A-2 (20 g, 129 mmol) in 40% HI (aq. 250 mL). The solution was heated to reflux at 140° C. for 2 days, the solution was quenched with 5N NaOH (aq.), and extracted with ethyl acetate. The organic layer was washed with brine, dried with anhydride $Na_2SO_4$, concentrated and purified by flash chromatography (petroleum ether:ethyl acetate 20:1) to give compound A-3 (5 g, yield=27%).

Preparation of Compound A-4 n-BuLi (17 mL, 2.5M) was slowly added to a solution of compound A-3 (5 g, 36 mmol) in THF (150 mL) at −78° C. The reaction was stirred at −78° C. for 1 h, then comp B (7.5 g, 43.2 mmol) was added slowly, the reaction was stirred at −78° C. for 2 h, then quenched with $NH_4Cl$ (aq), and extracted with ethyl acetate. The organic layer was washed with brine, dried with anhydride $Na_2SO_4$ and concentrated to give crude compound A-4 (10 g)

Preparation of Compound A-5

Iodoxybenzoic acid (IBX, 18 g, 63 mmol) was added to a solution of compound A-4 (10 g, 31.5 mmol) in 40 ml DMSO. The solution was stirred at 60° C. for 3 h, then cooled 0° C., quenched with $NaHCO_3$ (aq) and extracted 3.62-3.55 (1H, m), 3.56 (2H, J=5.6 Hz, t), 3.04 (2H, J=6.4 Hz, t), 2.00-1.98 (2H, m), 1.36 (6H, J=6.4 Hz, d); MS(ESI): 452[M+H]⁺.

Preparation of Compound 27

Burgess Reagent (80 mg, 0.33 mmol) was added to a solution of 33 (50 mg, 0.11 mmol) in THF (4 mL). The solution was stirred at RT overnight. The reaction was warmed 60° C. for 1 h and then the solution was concentrated and purified by prep-HPLC to give compound 27 (2 mg).

Using the above methods the following compounds can also be prepared (methods below table).

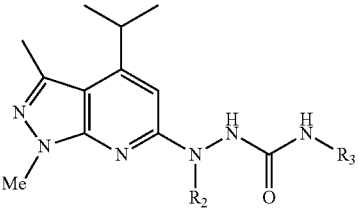

| Compound: | R₂ | R₃ |
|---|---|---|
| No 34 | —CH₂CH₂CH₂OH | 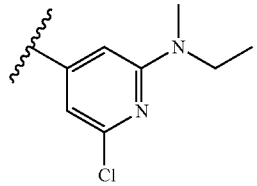 [SMILES: *c1cc(Cl)nc(N(C)CC)c1] |
| No 35 | —CH₂CH₂OH | 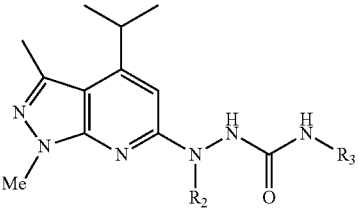 |
| No 36 | —CH₂CH₂OH | 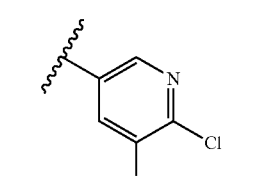 |
| No 37 | —CH₂CH₂OH | 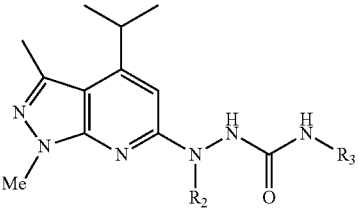 |
| No 38 | —CH₂CH₂OH | 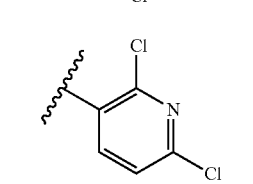 |

-continued

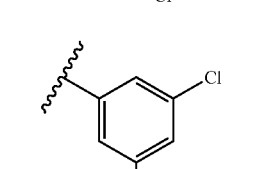

| Compound: | R₂ | R₃ |
|---|---|---|
| No 39 | —CH₂CH₂OH | 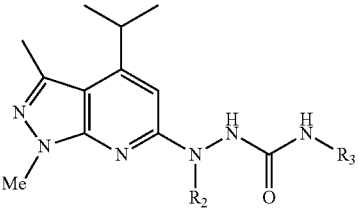 |
| No 40 | —CH₂CH₂OH | 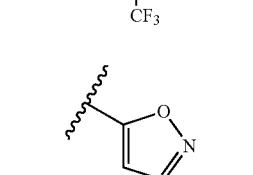 |
| No 41 | —CH₂CH₂OH | 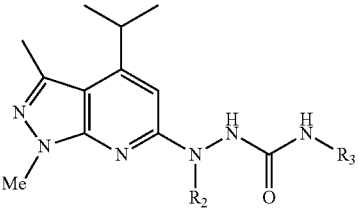 |
| No 42 | —CH₂CH₂OH | 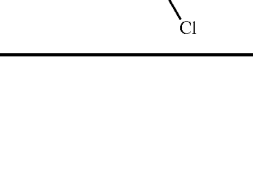 |
| No 43 | —CH₂CH₂OH | 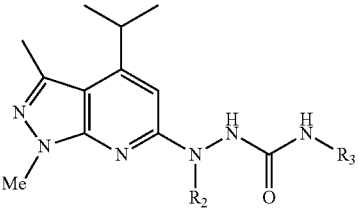 |
| No 44 | —CH₂CH₂OH |  |
| No 45 | —CH₂CH₂OH | 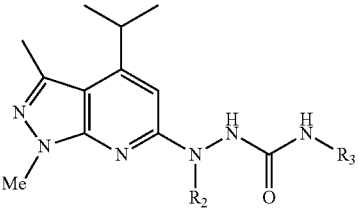 |

General Methods for Synthesis of Compounds 34-45

General Procedure for Acid to Isocyanate.

Method A.

The appropriate acid (1.0 eq, 0.5 mmol) was dissolved in freshly distilled Ethyl Acetate (5 mL) and the solution was cooled to 0° C. To this solution was added tri-ethylamine (1.3 eq, 0.65 mmol, 0.09 mL) followed by diphenylphosphoryl azide (1.1 eq, 0.55 mmol, 0.12 mL). The reaction was allowed to warm to room temperature and stirred overnight. It was then quenched with water and extracted (2×25 mL) with ethyl acetate. Organic layer was washed with water (20 mL), followed by brine (20 mL), dried with sodium sulfate, and concentrated to half the volume. Toluene (10 mL) was added and the remainder ethyl acetate was removed with the internal temperature of the rotovapor water bath not exceeding 35° C. The Toluene solution (10 mL, 0.5 mmol) was then heated under reflux for 3-4 h and monitored by TLC for completion. The solution was cooled to room temperature and used directly for the next reaction.

Method B.

The appropriate acid (1.0 eq, 0.5 mmol) was dissolved in dry THF (5 mL) with 2 drops of dry DMF. To this solution was added oxalyl chloride (1.3 eq, 0.65 mmol, 0.06 mL) dropwise. The solution was stirred for 1 h at rt and monitored by TLC for completion. Azidotrimethylsilane (2.0 eq, 1.0 mmol, 0.13 mL) was added, stirred for 2 h and monitored by TLC for completion. The reaction was quenched with water, concentrated and diluted with ethyl acetate (20 mL). The organic layer was washed with water (20 mL) and brine (20 mL), dried and concentrated to half the volume. Toluene (10 mL) was added and the remaining ethyl acetate was removed with the internal temperature of the rotovapor water bath not exceeding 35° C. The Toluene solution (10 mL, 0.5 mmol) was then refluxed for 3-4 h and monitored by TLC for completion. The solution was cooled to room temperature and used directly for the next reaction.

Synthesis Preparation of Acids 1 to 5

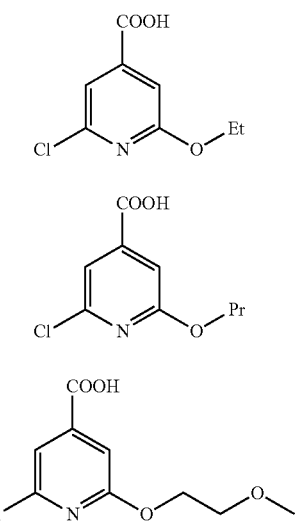

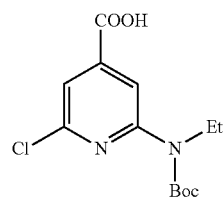

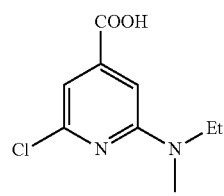

Synthesis of Acid 1

The synthesis of acid 1 is reported in the literature (PCT Int. Appl., 2012042433, 5 Apr. 2012, Didiuk, Mary Theresa et al. Preparation of pyrazolospiroketone acetyl-CoA carboxylase).

Synthesis of Acid 2

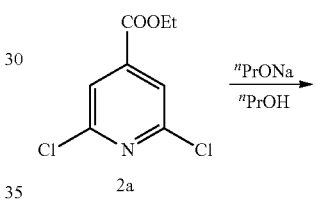

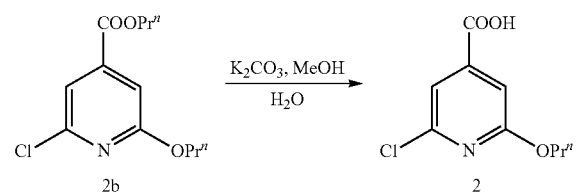

Preparation of Intermediate 2b:

To a solution of compound 2a (1.5 g, 6.84 mmol) in n-propanol (10 mL) was added sodium $^n$PrONa (3.4 mL, 2M) and stirred at 50° C. for 48 h. The solvent was removed under reduced pressure, diluted with ice (10 g), and extracted with ethyl acetate (3×10 mL). The combined extracts were dried over MgSO$_4$, filtered, and concentrated under reduced pressure provided (1.4 g, 79%) of compound 2b. $^1$H NMR (300 Hz, CDCl$_3$) δ 7.41 (s, 1H), 7.20 (s, 1H), 4.22-4.35 (m, 4H), 1.75-1.82 (m, 4H), 0.99-1.15 (m, 6H).

Preparation of Acid 2:

To a solution of compound 2b (1.48 g, 5.75 mmol) in methanol (15 mL), water (7 mL) was added potassium carbonate (1.6 g, 11.59 mmol) and stirred at rt for 16 h. The solvent was removed under reduced pressure, diluted with water (15 mL), acidified with KHSO$_4$, filter the solid, and dried (2, 910 mg, 74%). $^1$H NMR (300 Hz, CDCl$_3$) δ 8.21 (br s, 1H), 7.44 (s, 1H), 7.24 (s, 1H), 4.28 (t, J=6.6 Hz, 2H), 1.76-1.83 (m, 2H), 1.01 (t, J=7.2 Hz, 3H).

Synthesis of Acid 3

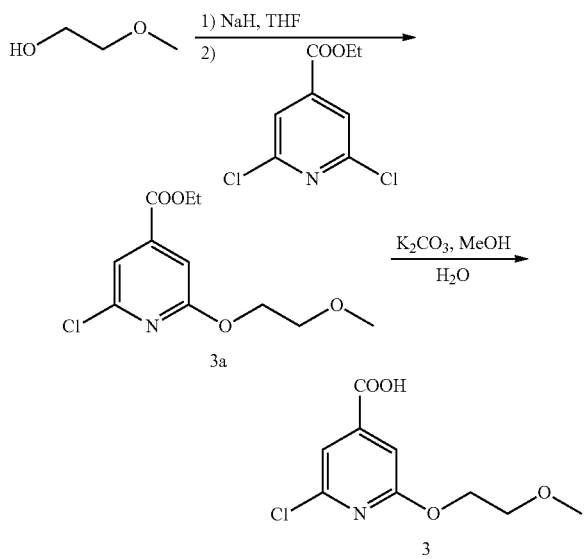

Preparation of Intermediate 3a:

To a solution of sodium hydride (115 mg, 4.79 mmol, 1.05 eq) in dry THF (10 mL) was added dropwise 2-methoxyethanol at 0° C. and stirred for 30 minutes. This solution was added to ethyl 2,6-dichloroisonicotinate (1.0 g, 4.57 mmol, 1.0 eq) in dry THF (5 mL) at room temperature and then heated at 50° C. overnight. The reaction was neutralized by addition of 2N HCl (2.5 mL, 5 mmol). The solvent was removed, added water (10 mL) and extracted with ethyl acetate (3×10 mL). The combined extracts were dried over MgSO$_4$, filtered, and concentrated under reduced pressure provided 3a. (600 mg, 51%) $^1$H NMR (MeOD): δ 7.42 (s, 1H), 7.22 (s, 1H), 4.46-4.35 (m, 4H), 3.75 (m, 2H), 3.40 (s, 3H), 1.40 (t, 3H).

Preparation of Acid 3:

To a solution of compound 3a (600 mg, 2.31 mmol) in methanol (10 mL), water (4 mL) was added potassium carbonate (635 mg, 4.6 mmol) and stirred at rt for 16 h. The solvent was removed under reduced pressure, diluted with water (10 mL), acidified with KHSO$_4$, and extracted with ethyl acetate (3×10 mL). The combined extracts were dried over MgSO$_4$, filtered, and concentrated under reduced pressure provided 3 (320 mg, 59%). $^1$H NMR (MeOD): δ 7.41 (s, 1H), 7.22 (s, 1H), 4.45 (t, 2H), 3.74 (t, 2H), 3.40 (s, 3H).

Synthesis of Acid 4

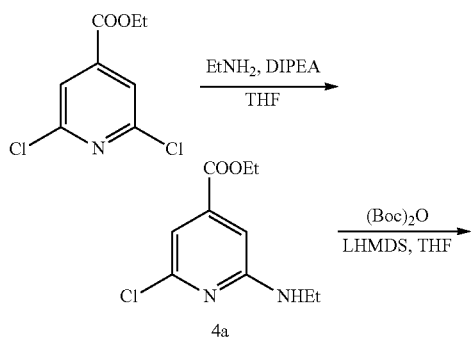

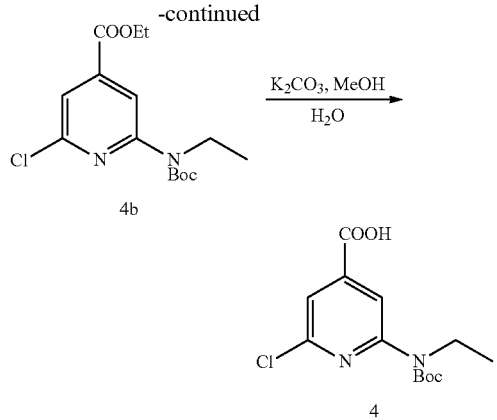

Preparation of Intermediate 4a:

To a solution of compound 2a (2.5 g, 10.9 mmol), ethyl amine (5.45 mL, 2M), DIPEA (2 mL) in THF (20 mL) were heated in a sealed tube at 75° C. for 16 h. The solvent was removed under reduced pressure, diluted with water (15 mL), and extracted with ethyl acetate (3×15 mL). The combined extracts were dried over MgSO$_4$, filtered, and concentrated under reduced pressure provided the crude compound. Further, purification by column chromatography using a silica gel column provided the desired compound 4a (450 mg, 17%) $^1$H NMR (300 Hz, CDCl$_3$) δ 7.08 (s, 1H), 6.80 (s, 1H), 4.40 (q, J=7.2, 14.3 Hz, 2H), 3.31 (q, J=7.2, 14.1 Hz, 2H), 1.39 (t, J=6.9 Hz, 3H), 1.24 (t, J=6.9 Hz, 3H).

Preparation of Intermediate 4b:

To a solution of compound 4a (400 mg, 1.68 mmol) in THF (5 mL) at −10° C. was added LHMDS (2 mL, 1M) slowly in drops. After 30 min, (Boc)$_2$O (440 mg, 2.01 mmol) in THF was added and slowly bring to rt and stirred for 30 min. The solvent was removed under reduced pressure, diluted with saturated NH$_4$Cl (10 mL), and extracted with ethyl acetate (3×10 mL). The combined extracts were dried over MgSO4, filtered, and concentrated under reduced pressure provided (1.4 g, 79%) of compound 4b. $^1$H NMR (300 Hz, CDCl$_3$) δ 8.19 (s, 1H), 7.52 (s, 1H), 4.40 (q, J=7.2, 14.4 Hz, 2H), 4.00 (q, J=7.2, 14.1 Hz, 2H), 1.54 (s, 9H), 1.37 (t, J=6.9 Hz, 3H), 1.23 (t, J=6.9 Hz, 3H).

Preparation of Acid 4:

To a solution of compound 4b (1.00 g, 2.95 mmol), in methanol (12 mL), water (3 mL) was added potassium carbonate (800 mg, 5.79 mmol) and stirred at rt for 16 h. The solvent was removed under reduced pressure, diluted with water (15 mL), acidified with KHSO$_4$, filter the solid, and dried to obtain the desired compound 4 (910 mg, 74%). $^1$H NMR (300 Hz, CDCl$_3$) δ 8.31 (s, 1H), 7.57 (s, 1H), 4.02 (q, J=7.2, 14.2 Hz, 2H), 1.55 (s, 9H), 1.25 (t, J=7.2 Hz, 3H).

Synthesis of Acid 5

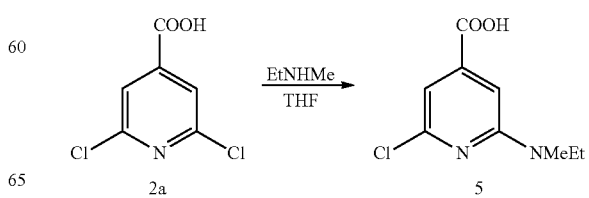

Preparation of Acid 5:

To a solution of compound 2a (1.0 g, 5.20 mmol), N-ethylmethylamine (1.5 g, 25.42 mmol), in water (3 mL) and heated to reflux for 48 h. The solvent was removed under reduced pressure. Triturating with IPE and hexane provided the desired compound 5 (300 mg, 27%). $^1$H NMR (300 Hz, CDCl$_3$) δ 11.90 (br s, 1H), 7.04 (s, 1H), 6.97 (s, 1H), 3.59 (q, J=6.9, 14.4 Hz, 2H), 4.00 (s, 3H), 1.17 (t, J=6.9 Hz, 3H).

General Procedure for the Reaction of Pyrazolopyridine Derivative Below with Isocyanates.

2-(1-(4-Isopropyl-1,3-dimethyl-1H-pyrazolo[3,4-b]pyridin-6-yl)hydrazinyl)ethan-1-ol

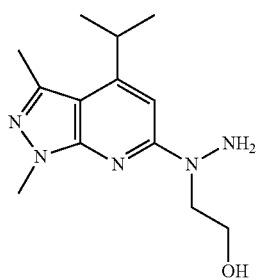 [SMILES: Cc1nn(C)c2nc(N(N)CCO)cc(C(C)C)c12]

A solution of hydrazine derivative (100 mg, 0.38 mmol) in dry THF (10 mL) was stirred at room temperature in which a solution of the appropriate isocyanate (~1.3 eq, 0.5 mmol) in toluene (10 mL) was added drop wise and stirred for 12 h or until completion by TLC monitoring. The crude reaction was concentrated and purified by column chromatography using 1:1 dichloromethane/ethyl acetate as the eluent to give the desired product.

Synthesis of Compound 34

N-(2,6-Dichloropyridin-4-yl)-2-(2-hydroxypropyl)-2-(4-isopropyl-1,3-dimethyl-1H-pyrazolo[3,4-b]pyridin-6-yl)hydrazine-1-carboxamide (Compound 34)

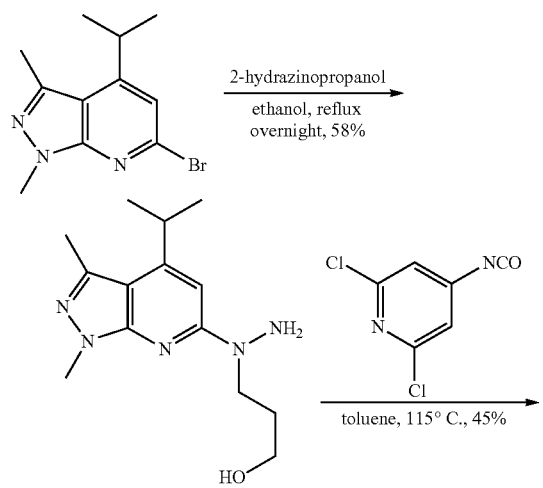

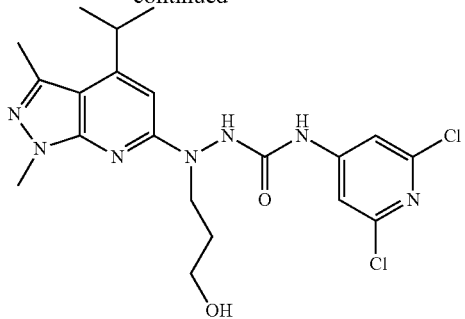

Compound 34

2-(1-(4-Isopropyl-1,3-dimethyl-1H-pyrazolo[3,4-b]pyridin-6-yl)hydrazinyl)propan-1-ol

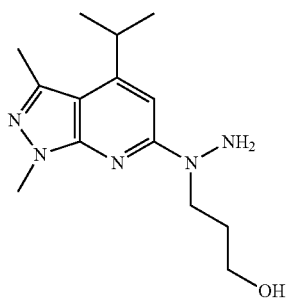 [SMILES: Cc1nn(C)c2nc(N(N)CCCO)cc(C(C)C)c12]

2-Hydrazinopropanol (3.35 g, 37.2 mmol) was added to a solution of 1H-6-bromo-4-isopropyl-1,3-dimethylpyrazolo[3, 4-b] pyridine (500 mg, 1.87 mmol) in ethanol (2.5 mL) and heated under reflux overnight. After cooling, it was stirred for 4 h in an ice bath. The crude material was filtered and the obtained solid was triturated with a 50% aqueous ethanol (5 mL), filtered and dried under reduced pressure at 60° C. to give 2-(1-(4-Isopropyl-1,3-dimethyl-1H-pyrazolo[3,4-b]pyridin-6-yl)hydrazinyl)propan-1-ol as white solid, B-2 (300 mg, 58% yield).

$^1$H 300 MHz NMR (CDCl$_3$) δ 6.89 (1H, s), 4.95 (2H, bs), 4.28 (1H, bs), 3.99 (2H, m), 3.85 (3H, s), 3.58 (2H, t), 3.48 (1H, m), 2.57 (3H, s), 1.93 (2H, m), 1.33 (3H, s), 1.31 (3H, s).

Compound 34

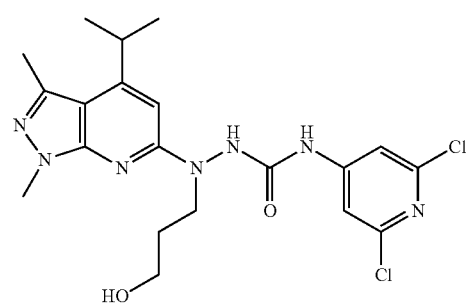 [SMILES: Cc1nn(C)c2nc(N(CCCO)NC(=O)Nc3cc(Cl)nc(Cl)c3)cc(C(C)C)c12]

Method A (80 mg, 45%, 3 steps) $^1$H 300 MHz NMR (CDCl$_3$+MeOD-4) δ 7.47 (2H, s), 6.52 (1H, s), 4.06 (2H, bm) 3.96-3.80 (2H, bm), 3.84 (3H, s), 3.44 (2H, m), 3.39 (1H, bs), 2.51 (3H, s), 1.24 (6H, d). ESI+(M+H) m/z=466.1

Compound 35

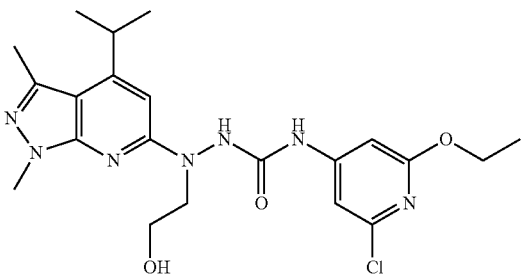

Method A (75 mg, 43%, 3 steps) ¹H 300 MHz NMR (CDCl₃) δ 8.91 (1H, s), 7.06 (1H, s), 6.85 (1H, s), 6.65 (1H, s), 6.60 (1H, s) 4.45 (1H, bs), 4.30 (2H, qt), 4.16 (2H, m), 3.90 (3H, s) 3.51 (2H, m), 2.80 (1H, bs) 2.60 (3H, s), 1.31 (6H, m) 1.29 (3H, m). ESI+(M+H) m/z=462.1

Compound 36

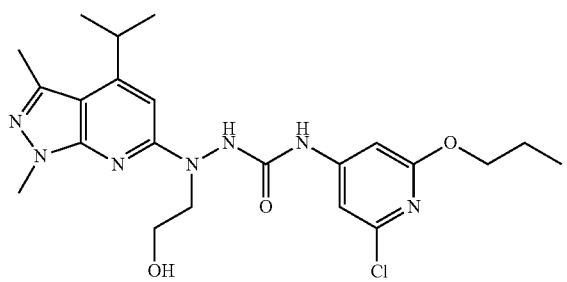 [SMILES: CCCOc1cc(NC(=O)NN(CCO)c2cc(C(C)C)c3c(C)nn(C)c3n2)cc(Cl)n1]

Method A (80 mg, 45%, 3 steps) ¹H 300 MHz NMR (CDCl₃) δ 8.99 (1H, s), 7.05 (1H, s), 6.87 (1H, s), 6.81 (1H, s), 6.60 (1H, s) 4.45 (1H, bs), 4.160 (2H, t), 4.10 (2H, m), 3.87 (3H, s) 3.48 (2H, m), 3.20 (1H, bs) 2.59 (3H, s), 1.75 (2H, m) 1.30 (6H, d) 0.97 (3H, t). ESI+(M+H) m/z=476.1

Compound 37

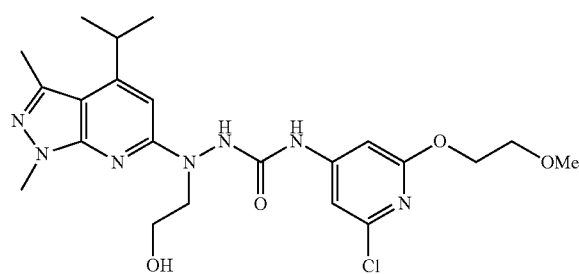 [SMILES: COCCOc1cc(NC(=O)NN(CCO)c2cc(C(C)C)c3c(C)nn(C)c3n2)cc(Cl)n1]

Method A (80 mg, 44%, 3 steps) ¹H 400 MHz NMR (CDCl₃) δ 8.91 (1H, s), 7.11 (1H, s), 6.89 (1H, s), 6.62 (1H, s), 6.58 (1H, s) 4.55 (1H, bs), 4.51 (2H, m), 4.09 (2H, m), 3.91 (3H, s), 3.67 (2H, m) 3.49 (2H, m), 3.39 (3H, s), 2.71 (1H, bs) 2.59 (3H, s), 1.30 (6H, d). ESI+(M+H) m/z=492.1

Compound 38-Boc

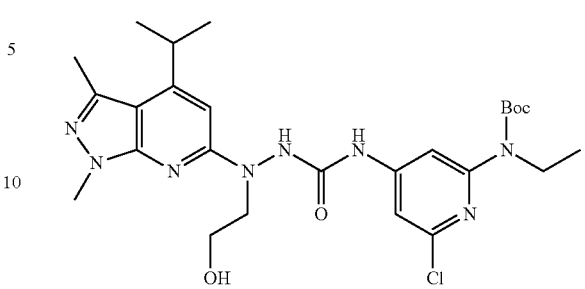

Method A (120 mg, 56%, 3 steps) ¹H 400 MHz NMR (CDCl₃) δ 8.96 (1H, s), 7.58 (2H, d), 6.81 (1H, bs), 6.62 (1H, s), 4.49 (1H, bs), 4.17-4.06 (2H, bm) 3.96 (2H, m), 3.91 (3H, s), 3.48 (2H, m), 3.03 (1H, bs), 2.62 (3H, s), 1.48 (9H, s), 1.30 (6H, d), 1.17 (3H, t). ESI+(M+H) m/z=561.2

Compound 38—HCl Salt

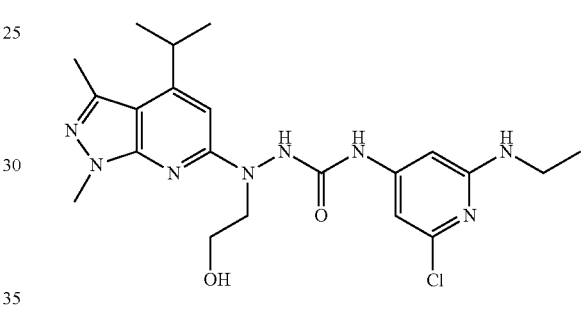

The above Boc derivative above was dissolved in dichloromethane (1 mL) cooled to 0-5° C. in an ice bath and added 2M HCl solution in ether (1 mL) and stirred overnight. The solid obtained was filtered, dried in vacuum oven to yield 60 mg of the hydrochloride salt. ¹H 400 MHz NMR (MeOD-4) δ 7.31 (1H, s), 6.99 (1H, s), 6.71 (1H, bs), 4.49 (1H, bs), 4.09-3.99 (2H, bm) 3.96 (2H, m), 3.93 (3H, s), 3.67 (1H, m), 3.53 (2H, m), 3.38 (2H, m), 2.64 (3H, s), 1.32 (6H, d) 1.12 (3H, t). ESI+(M+H) m/z=461.1

Compound 39

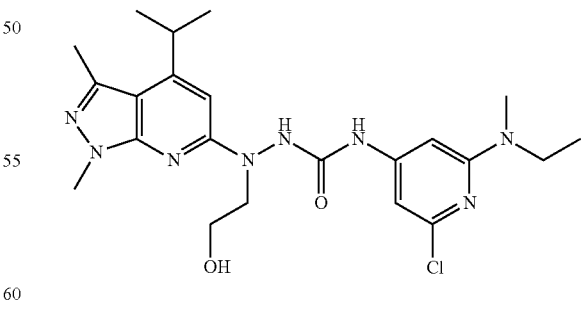

Method A (110 mg, 61%, 3 steps) ¹H 400 MHz NMR (DMSO) δ 9.47 (1H, s), 8.96 (1H, bs), 6.88 (1H, bs), 6.61 (1H, s), 6.49 (1H, s), 5.38, 4.73 (1H, bs), 4.17-3.86 (2H, bm) 3.80 (3H, s), 3.80-3.71 (2H, bm), 3.45 (2H, m), 2.89 (3H, s), 2.50 (3H, s), 1.23, (6H, d), 1.03 (3H, t). ESI+(M+H) m/z=475.1

Compound 40

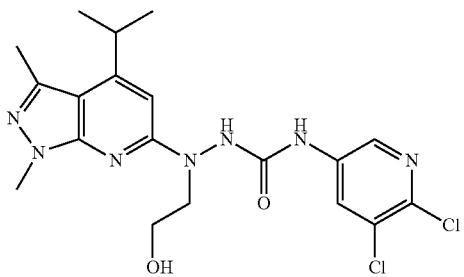

Method B (55 mg, 32%, 3 steps) $^1$H 300 MHz NMR (CDCl$_3$) δ 9.08 (1H, s), 8.35 (1H, s), 8.23 (1H, s), 6.70 (1H, s), 6.61 (1H, s), 4.49 (1H, bs), 4.17-4.06 (2H, bm), 3.91 (3H, s), 3.49 (2H, m), 3.11 (1H, bs), 2.60 (3H, s), 1.30 (6H, d). ESI+(M+H) m/z=452.1

Compound 41

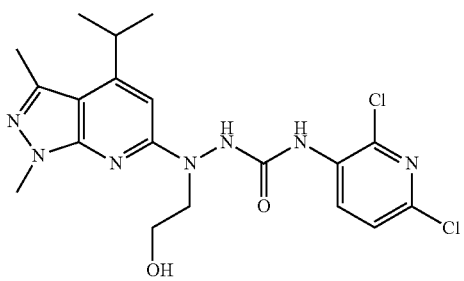 [SMILES: Cc1nn(C)c2nc(N(CCO)NC(=O)Nc3ccc(Cl)nc3Cl)cc(C(C)C)c12]

Method A (95 mg, 55%, 3 steps) $^1$H 400 MHz NMR (CDCl$_3$) δ 9.08 (1H, s), 8.36 (1H, d), 8.22 (1H, d), 6.71 (1H, bs), 6.62 (1H, s), 4.29 (1H, bs), 4.2-4.17 (2H, bm) 3.96 (2H, m), 3.451 (2H, m), 3.12 (1H, bs), 2.60 (3H, s), 1.32 (6H, d). ESI+(M+H) m/z=452.1

Compound 42

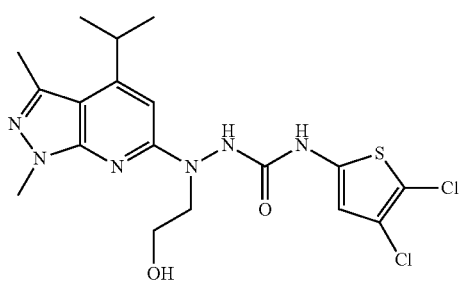 [SMILES: Cc1nn(C)c2nc(N(CCO)NC(=O)Nc3cc(Cl)c(Cl)s3)cc(C(C)C)c12]

Method A (45 mg, 26%, 3 steps) $^1$H 300 MHz NMR (CDCl$_3$) δ 9.54 (1H, s), 6.81 (1H, bs), 6.60 (1H, s), 6.25 (1H, s), 4.45 (1H, bs), 4.11-4.08 (2H, bm) 3.84 (3H, s), 3.49 (2H, m), 2.89 (1H, bs), 2.60 (3H, s), 1.30 (6H, d). ESI+(M+H) m/z=457.0

Compound 43)

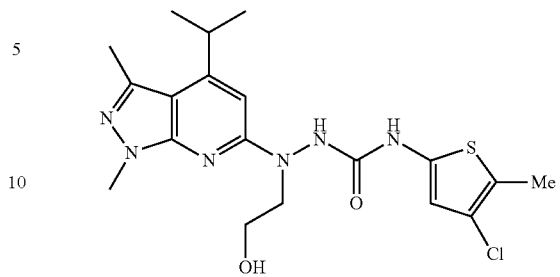

Method B (90 mg, 54%, 3 steps) $^1$H 300 MHz NMR (CDCl$_3$+MeOD-4) δ 6.49 (1H, bs), 6.21 (1H, s), 4.19-4.06 (2H, bm) 3.83 (3H, s), 3.48-3.38 (2H, bm) 3.35 (1H, m), 2.47 (3H, s), 2.16 (3H, s), 1.19 (6H, d). ESI+(M+H) m/z=437.1

Compound 44

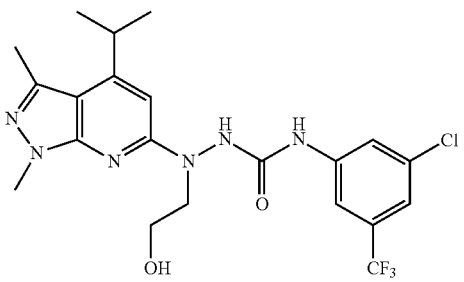 [SMILES: Cc1nn(C)c2nc(N(CCO)NC(=O)Nc3cc(Cl)cc(C(F)(F)F)c3)cc(C(C)C)c12]

Method A (110 mg, 60%, 3 steps) $^1$H 300 MHz NMR (CDCl$_3$+MeOD-4) δ 9.18 (1H, s), 7.76 (1H, s), 7.61 (1H, s), 7.19 (1H, s), 6.59 (1H, s), 4.43 (1H, bs), 4.07-3.92 (2H, bm), 3.85 (3H, s), 3.60-3.48 (2H, m), 2.54 (3H, s), 1.27 (6H, d). ESI+(M+H) m/z=485.1

Compound 45

Method B (90 mg, 58%, 3 steps) $^1$H 400 MHz NMR (CDCl$_3$+MeOD-4) δ 6.50 (1H, bs), 6.22 (1H, s), 4.34 (1H, bs), 4.17-4.06 (2H, bm), 3.82 (3H, s), 3.43 (2H, m), 2.52 (3H, s), 1.26 (6H, d). ESI+(M+H) m/z=408.1

In Vitro Binding Affinities

A number of compounds set forth above according to the present invention were tested to determine the binding affinity for S1P$_2$ and S1P$_5$ receptors (see below).

Antagonist percentage inhibition determinations were obtained by assaying sample compounds and referencing the control (EC$_{80}$) wells for each profiled (GPCR) which evaluated binding to S1P$_2$ and S1P$_5$ receptors. The samples were run using a single addition assay protocol. The protocol design is as follows.

I. Master Stock Solution

Unless specified otherwise, the sample compounds were diluted in 100% anhydrous DMSO including all dilutions. The compounds were tested as the citrate salt (1 equivalent per molecule). If the sample compound is provided in a different solvent all master stock dilutions are performed in the specified solvent. All control wells contained identical solvent final concentrations as the sample compound wells.

II. Compound Plate Assay

The sample compounds were transferred from a master stock solution into a daughter plate that was used in the assay. Each sample compound was diluted into an assay buffer (1×HBSS with 20 mM HEPES, 2.5 mM Probenecid, and 0.4% Free Fatty Acid BSA) at an appropriate concentration to obtain final specified concentrations.

III. Antagonist Assay Format

Using the $EC_{80}$ values that were determined real-time, stimulated all pre-incubated sample compounds and reference antagonists (if applicable) were compared with the $EC_{80}$ values of reference agonist. These were read for 180 seconds using the FLIPR$^{TETRA}$ (This assay added reference agonist to respective wells-then fluorescences measurements were collected to calculate $IC_{50}$ values). All plates were subjected to appropriate baseline corrections. Once baseline corrections were processed, maximum fluorescence values were exported and data manipulated to calculate percentage activation, percentage inhibition and Z'. The results are in the table below, and show that these compounds unexpectedly bind to both the $S1P_2$ and $S1P_5$ receptors

| Compound | Structure | $S1P_2$ $IC_{50}$ | $S1P_5$ $IC_{50}$ |
|---|---|---|---|
| JTE013 | 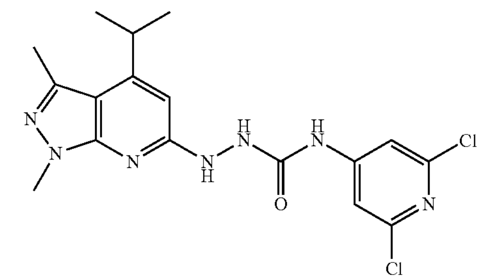 [SMILES: Cc1nn(C)c2nc(NNC(=O)Nc3cc(Cl)nc(Cl)c3)cc(C(C)C)c12] | 11 nM | 1.3 nM |
| 1. | 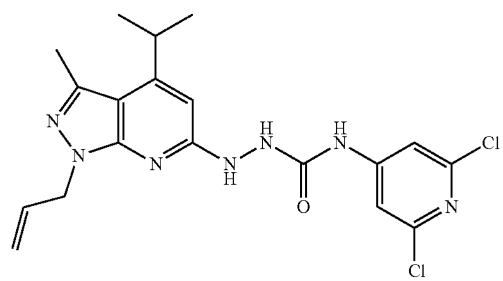 [SMILES: C=CCn1nc(C)c2c(C(C)C)cc(NNC(=O)Nc3cc(Cl)nc(Cl)c3)nc21] | 1.2 nM | 2.2 nM |
| 2. | 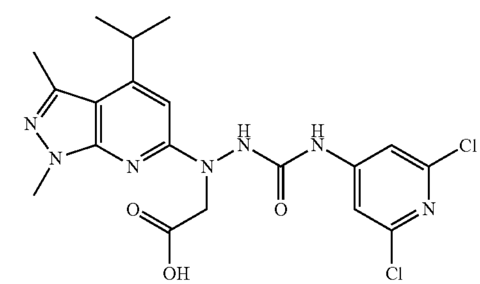 [SMILES: Cc1nn(C)c2nc(N(CC(=O)O)NC(=O)Nc3cc(Cl)nc(Cl)c3)cc(C(C)C)c12] | 11 nM | 3.2 nM |
| 3. | 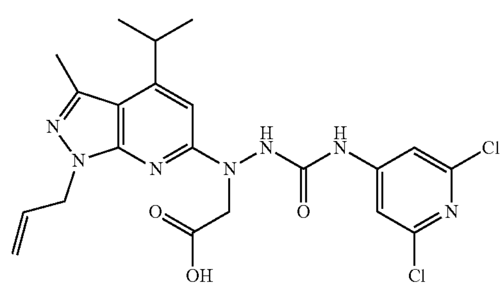 [SMILES: C=CCn1nc(C)c2c(C(C)C)cc(N(CC(=O)O)NC(=O)Nc3cc(Cl)nc(Cl)c3)nc21] | 3 μM | 5.7 μM |

-continued

| Compound | Structure | S1P$_2$ IC$_{50}$ | S1P$_5$ IC$_{50}$ |
|---|---|---|---|
| 4. | 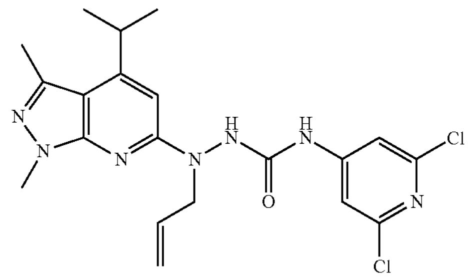 [SMILES: C=CCN(NC(=O)Nc1cc(Cl)nc(Cl)c1)c1cc(C(C)C)c2c(C)nn(C)c2n1] | 52 nM | 110 nM |
| 5. | 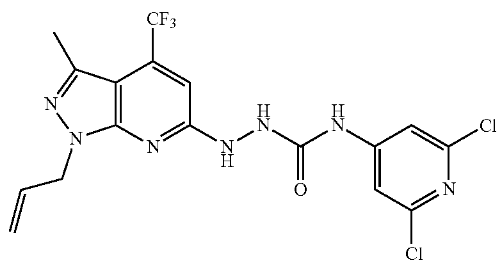 [SMILES: C=CCn1nc(C)c2c(C(F)(F)F)cc(NNC(=O)Nc3cc(Cl)nc(Cl)c3)nc21] | >10 μM | >10 μM |
| 6. | 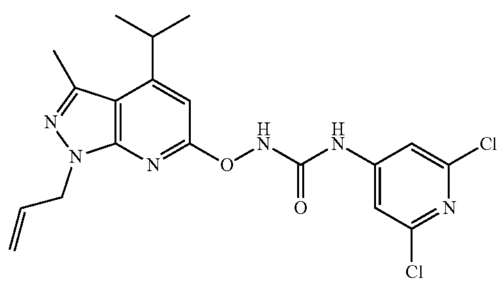 [SMILES: C=CCn1nc(C)c2c(C(C)C)cc(ONC(=O)Nc3cc(Cl)nc(Cl)c3)nc21] | 52 nM | 8.7 nM |
| 9. | 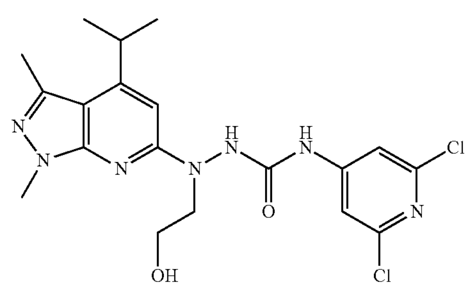 [SMILES: Cc1nn(C)c2nc(N(CCO)NC(=O)Nc3cc(Cl)nc(Cl)c3)cc(C(C)C)c12] | 7.0 nM | 20.9 nM |
| 27. | 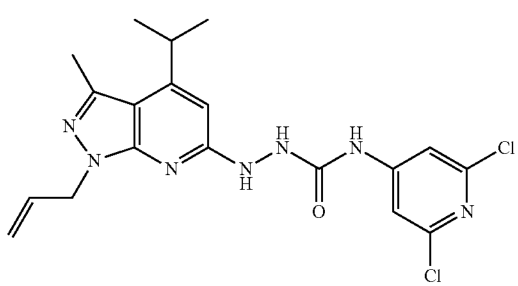 [SMILES: C=CCn1nc(C)c2c(C(C)C)cc(NNC(=O)Nc3cc(Cl)nc(Cl)c3)nc21] | 75 nM | 165 nM |

-continued

| Compound | Structure | S1P$_2$ IC$_{50}$ | S1P$_5$ IC$_{50}$ |
|---|---|---|---|
| 33. | 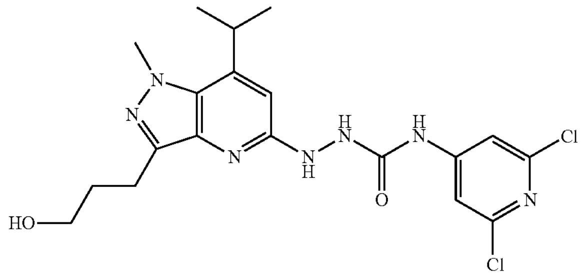 [SMILES: CC(C)c1cc(NNC(=O)Nc2cc(Cl)nc(Cl)c2)nc2c(CCCO)nn(C)c12] | 5.0 nM | <10 nM incomplete curve |
| 34. | 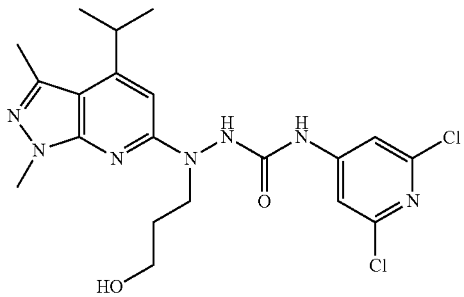 [SMILES: Cc1nn(C)c2nc(N(CCCO)NC(=O)Nc3cc(Cl)nc(Cl)c3)cc(C(C)C)c12] | 19 nM | 12 nM |
| 35. | 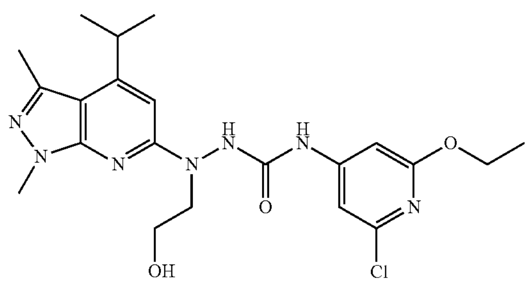 [SMILES: CCOc1cc(NC(=O)NN(CCO)c2cc(C(C)C)c3c(C)nn(C)c3n2)cc(Cl)n1] | 29 nM | 13 nM |
| 36. | 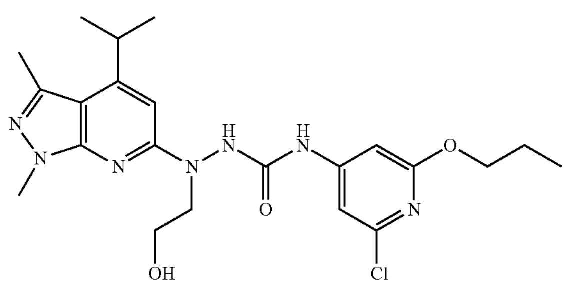 [SMILES: CCCOc1cc(NC(=O)NN(CCO)c2cc(C(C)C)c3c(C)nn(C)c3n2)cc(Cl)n1] | 10 nM | 33 nM |
| 37. | 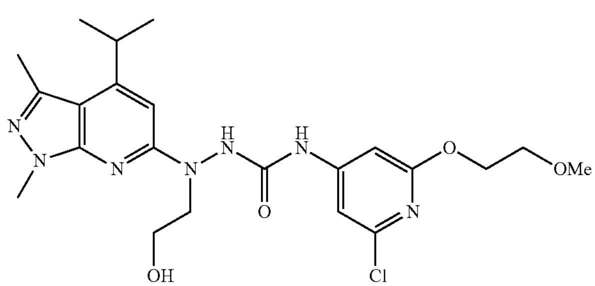 [SMILES: COCCOc1cc(NC(=O)NN(CCO)c2cc(C(C)C)c3c(C)nn(C)c3n2)cc(Cl)n1] | 160 nM | >10 μM |

-continued

| Compound | Structure | S1P$_2$ IC$_{50}$ | S1P$_5$ IC$_{50}$ |
|---|---|---|---|
| 38. | 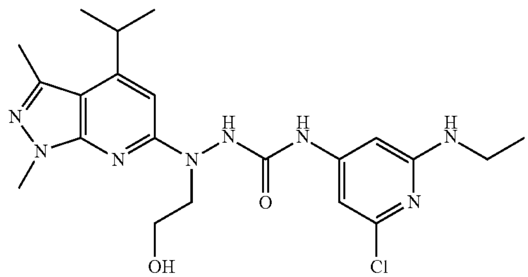 [SMILES: CCNc1cc(NC(=O)NN(CCO)c2cc(C(C)C)c3c(C)nn(C)c3n2)cc(Cl)n1] | 4 nM | 4.6 nM |
| 39. | 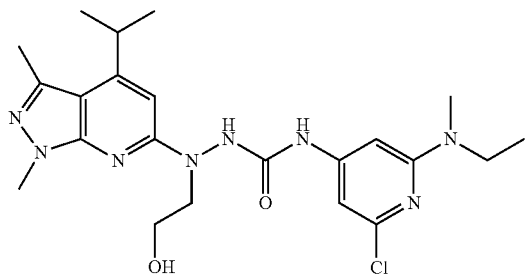 [SMILES: CCN(C)c1cc(NC(=O)NN(CCO)c2cc(C(C)C)c3c(C)nn(C)c3n2)cc(Cl)n1] | 19 nM | 40 nM |
| 40. | 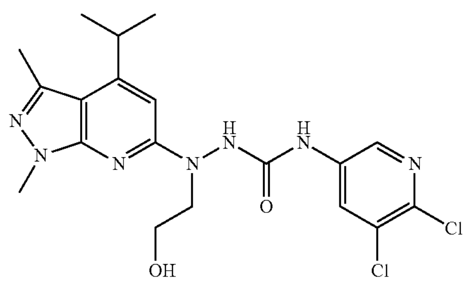 [SMILES: Cc1nn(C)c2nc(N(CCO)NC(=O)Nc3cnc(Cl)c(Cl)c3)cc(C(C)C)c12] | 300 nM | >10 μM |
| 41. | 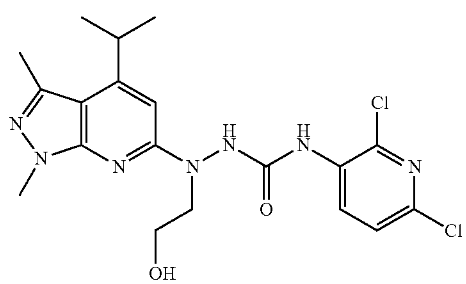 [SMILES: Cc1nn(C)c2nc(N(CCO)NC(=O)Nc3ccc(Cl)nc3Cl)cc(C(C)C)c12] | >10 μM | >10 μM |
| 42. | 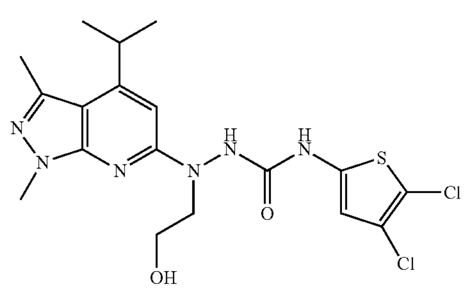 [SMILES: Cc1nn(C)c2nc(N(CCO)NC(=O)Nc3cc(Cl)c(Cl)s3)cc(C(C)C)c12] | 64 nM | 290 nM |

-continued

| Compound | Structure | S1P$_2$ IC$_{50}$ | S1P$_5$ IC$_{50}$ |
|---|---|---|---|
| 43. | 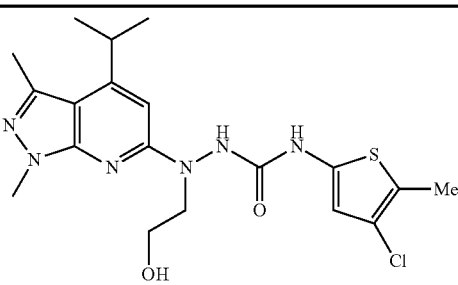 | 360 nM | >10 μM |
| 44. | 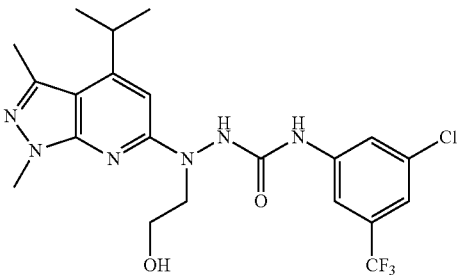 [SMILES: Cc1nn(C)c2nc(N(CCO)NC(=O)Nc3cc(Cl)cc(C(F)(F)F)c3)cc(C(C)C)c12] | >120 nM | 74 nM |
| 45. | 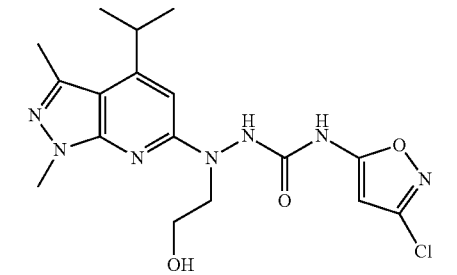 [SMILES: Cc1nn(C)c2nc(N(CCO)NC(=O)Nc3cc(Cl)no3)cc(C(C)C)c12] | >10 μM | >10 μM |

Blood Concentration Data for JTE013 and Cmpd-1

In order to determine the pharmacokinetics of of JTE013 and compound 1, each in 3 normal mice. 1 mg/kg of the compound was injected by IV and blood was withdrawn at the times in table 1. The amount of starting compound was quantified by a standard curve using MS/MS determinations.

TABLE 1

Blood concentrations of the JTE013 control versus time following 1 mg/kg i.v. administration of JTE013 to 3 mice (M01-M03).

| Sample Collection | JTE013 Blood Concentrations (ng/mL) | | | |
|---|---|---|---|---|
| Time (h) | M01 | M02 | M03 | Mean – S.D. |
| Pre-dose (0) | No Peak | No Peak | No Peak | n/a |
| 0.0833 | 282 | 231 | 302 | 272 ± 36.6 |
| 0.25 | 109 | 78.3 | 95.8 | 94.4 ± 15.4 |
| 0.5 | 44.4 | 33.8 | 40.4 | 39.5 ± 5.35 |
| 1 | 11.8 | 14.4 | 13.4 | 13.2 ± 1.31 |
| 2 | 2.72 | 3.16 | 3.12 | 3.00 ± 0.243 |
| 4 | 1.01 | 0.732$^c$ | 0.771$^c$ | 0.838 ± 0.151 |
| 6 | 0.805$^c$ | 0.496$^c$ | 0.643$^c$ | 0.648 ± 0.155 |
| 12 | BLQ | BLQ | 0.547$^c$ | n/a |

$^a$ NP denotes no peak.
$^b$ n/a denotes not applicable.
$^c$ Value is greater than 50% of LLOQ (>0.5 ng/mL) and was included in calculations.
$^d$ BLQ denotes below lower level of quantification (LLOQ = 1 ng/mL).

TABLE 2

Blood concentrations of Cmpd-1 versus time following 1 mg/kg i.v. administration of EDG-1 to 3 mice (M04-M06).

| Sample Collection | Cmpd-1 Plasma Concentrations (ng/mL) | | | |
|---|---|---|---|---|
| Time (h) | M04 | M05 | M06 | Mean – S.D. |
| Pre-dose (0) | No Peak | No Peak | No Peak | n/a |
| 0.0833 | 188 | 152 | 143 | 161 ± 23.8 |
| 0.25 | 48.3 | 51.2 | 46.3 | 48.6 ± 2.46 |
| 0.5 | 14.9 | 22.8 | 17.1 | 18.3 ± 4.08 |
| 1 | 5.11 | 7.90 | 6.44 | 6.48 ± 1.40 |
| 2 | 1.13 | 3.12 | 2.96 | 2.40 ± 1.11 |
| 4 | BLQ | 2.22 | 1.98 | 2.10 (n = 2) |
| 6 | BLQ | 2.55 | 2.25 | 2.40 (n = 2) |
| 12 | BLQ | 1.36 | 2.04 | 1.70 (n = 2) |

$^a$ NP denotes no peak.
$^b$ n/a denotes not applicable.
$^c$ BLQ denotes below lower level of quantification (LLOQ = 1 ng/mL).

TABLE 3

Compound 1 blood concentrations versus time following 1 mg/kg i.v. administration of Compound 1 to group of 3 mice (M04-M06).

| Parameter | Units | Estimate M01[a] | M02[a] | M03 | Mean – S.D. |
|---|---|---|---|---|---|
| $C_0$ | ng/mL | 453 | 397 | 536 | 462 ± 70.1 |
| Terminal half-life | h | 6.11 | 3.56 | 18.7 | 9.45 ± 8.09 |
| $AUC_{0\text{-}tlast}$ | h*ng/mL | 102 | 85.6 | 108 | 98.4 ± 11.4 |
| $AUC_{0\text{-}inf}$ | h*ng/mL | 109 | 88.2 | 122 | 107 ± 17.2 |
| $AUC_{0\text{-}inf}$ Extrapolated | % | 6.50 | 2.89 | 12.1 | 7.15 ± 4.61 |
| CL | L/h/kg | 9.15 | 11.3 | 8.18 | 9.56 ± 1.62 |
| $AUMC_{0\text{-}tlast}$ | h²*ng/mL | 48.1 | 42.8 | 78.0 | 56.3 ± 19.0 |
| $AUMC_{0\text{-}inf}$ | h²*ng/mL | 153 | 71.2 | 652 | 292 ± 314 |
| $AUMC_{0\text{-}inf}$ Extrapolated | % | 68.6 | 39.9 | 88.0 | 65.5 ± 24.2 |
| $MRT_{0\text{-}tlast}$ | h | 0.471 | 0.500 | 0.725 | 0.565 ± 0.139 |
| $MRT_{0\text{-}inf}$ | h | 1.40 | 0.807 | 5.33 | 2.51 ± 2.46 |
| $V_{ss}$ | L/kg | 12.8 | 9.16 | 43.6 | 21.9 ± 18.9 |

[a]Terminal half-life was estimated from the last 2 measurable concentrations.

TABLE 3

Estimated pharmacokinetics parameters for Cmpd-1 in blood following 1 mg/kg i.v. administration of EDG-1 to 3 mice (M04-M06).

| Parameter | Units | Estimate M04 | M05 | M06 | Mean – S.D. |
|---|---|---|---|---|---|
| $C_0$ | ng/mL | 371 | 262 | 251 | 295 ± 66.2 |
| Terminal half-life | h | NC | 9.08 | 41.7 | 25.4 (n = 2) |
| $AUC_{0\text{-}tlast}$ | h*ng/mL | 53.9 | 74.6 | 69.5 | 66.0 ± 10.8 |
| $AUC_{0\text{-}inf}$ | h*ng/mL | NC | 92.4 | 192 | 142 (n = 2) |
| $AUC_{0\text{-}inf}$ Extrapolated | % | NC | 19.3 | 63.8 | 41.5 (n = 2) |
| CL | L/h/kg | NC | 10.8 | 5.20 | 8.01 (n = 2) |
| $AUMC_{0\text{-}tlast}$ | h²*ng/mL | 12.7 | 157 | 166 | 112 ± 86.0 |
| $AUMC_{0\text{-}inf}$ | h²*ng/mL | NC | 604 | 9010 | 4810 (n = 2) |
| $AUMC_{0\text{-}inf}$ Extrapolated | % | NC | 74.1 | 98.2 | 86.1 (n = 2) |
| $MRT_{0\text{-}tlast}$ | h | 0.236 | 2.10 | 2.39 | 1.58 (n = 2) |
| $MRT_{0\text{-}inf}$ | h | NC | 6.53 | 46.9 | 26.7 (n = 2) |
| $V_{ss}$ | L/kg | NC | 70.7 | 244 | 157 (n = 2) |

[a] Terminal half-life was estimated from the last 2 measurable concentrations.
[b] NC denotes not calculable due to truncated nature of PK curve.

The blood concentrations reported above that were measured for JTE013 and compound-1 following 1 mg/kg i.v. administration to the mice shown above clearly demonstrates that since mice that were administered compound 1 had the highest drug blood levels over time, it demonstrates a greater binding affinity for the $SP_1$ and $SP_2$ receptors and hence greater efficacy in the treatment of neoplastic diseases through the hinderance and prevention of cellular proliferation, migration, and morphogenesis to form new capillary networks necessary for the growth and expansion of cancer cells. In its' ability to be maintained at higher blood levels for longer periods of time, the greater the likelihood the compounds will have an affinity for the receptors and bind thereto In Vitro ADME-Tox Summary In order to get additional information on the protein binding and metabolism of JTE013 and compound 1 and compound 2, in vitro plasma protein binding and microsomal intrinsic clearance studies were completed. The results are below.

TABLE 5

Plasma Protein Binding Summary

| Compound | Test concentration | Species | mean fraction bound (%) |
|---|---|---|---|
| Warfarin | 5 nM | mouse | 92.1 |
| Propanolol | 5 nM | mouse | 87.4 |
| Compound 1 | 5 nM | mouse | 99.9 |
| Compound 2 | 5 nM | mouse | 77.0 |
| JTE013 | 5 nM | mouse | 99.7 |

TABLE 6

Microsomal Intrinsic Clearance Summary

| Compound | test Conc. (μM) | species | NADPH-dependent Clint[a] (μl min⁻¹ mg⁻¹) | NADPH-dependent T1/2[b] (min) | NADPH-free Clint[a] (μl min⁻¹ mg⁻¹) | NADPH-free T1/2[b] (min) |
|---|---|---|---|---|---|---|
| Verapamil | 1 | mouse | 398 | 5.8 | 9 | >180 |
| Warfarin | 1 | mouse | 15 | 157 | 10 | >180 |
| Compound 1 | 1 | mouse | 1172 | 2 | 48 | 48 |
| Compound 2 | 1 | mouse | 20 | 113 | 9 | >180 |
| JTE013 | 1 | mouse | 770 | 3.0 | 22 | 105 |

[a]Microsomal intrinsic clearance
[b]Half-life

Verapamil is a metabolized control, while Warfarin is a non-metabolized control.

From the initial in vitro ADME toxicology study using plasma protein binding and microsomal intrinical clearance, it's clear that the known control JTE013 and compound 1 behave very similarly in both assays, while compound 2 was much more stable in liver microsomes and had lower plasma protein binding. To further clarify the properties of these molecules the clearance of the compounds were studied following intravenous injection in mice. Compound 1 had substantially improved pharmacokinetics, over JTE013, which was better than compound 2 (see area under curves). With greater potency for receptor binding and higher drug plasma levels after 2 h, one would expect greater in vivo efficacy for compound 1. The differences between the in vivo metabolism and pharmacokinetics of the three compounds are noteworthy. The strong protein binding of compound 1 must offset the metabolism in the liver. The free carboxyl group of compound 2 may lead to glucoronylation and more rapid excretion than the in vitro metabolism study might suggest, or that the decreased protein binding is deleterious Pharmaceutical compositions comprising the above-listed S1P receptor agonists may comprise additional pharmacological agents used in the treatment of disorders relating to vascular permeability and vascular endothelial cell apoptosis. Suitable additional pharmacological agents include, for example, cytotoxic agents, chemotherapeutic agents, hormones, steroidal anti-inflammatory drugs (e.g., prednisone, corticosteroids, and the like), non-steroidal anti-inflammatory drugs (e.g., NSAIDs, aspirin, acetaminophen, and the like); and combinations comprising one or more of the foregoing additional pharmacological agents.

Pharmaceutical compositions may be formulated using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by means known in the art with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); wetting agents (e.g., sodium lauryl sulfate); and combinations comprising one or more of the foregoing excipients. The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); preservatives (e.g., methyl or propyl-p-hydroxybenzoates or sorbic acid); and combinations comprising one or more of the foregoing additives. The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated by techniques known in the art. For administration by inhalation, the compounds are conveniently delivered in the form of an aerosol spray presentation from pressurized packs or a nebuliser, with the use of a suitable propellant, for example, di-chloro-difluoromethane, tri-chloro-fluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain form ulatory agents such as suspending, stabilizing, and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

It is contemplated herein then, that the $S1P_2$ receptor selective antagonist compounds of the present invention can be formulated as compositions described above in pharmaceutically acceptable amounts for the treatment of angiogenic eye disorders, neoplastic eye disease and blindness as well as for the treatment of fibrotic disorders of the lung, kidney, liver and skin diseases through the administration of a pharmaceutically acceptable amount thereof in any one of a number of the carrier compositions described above.

I claim:

1. A sphingosine-1-phosphate receptor 2 ($S1P_2$) antagonist compound of the formula:

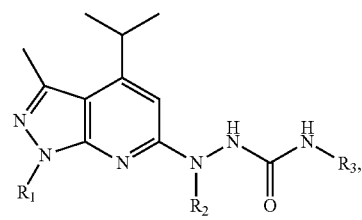

wherein:
$R_1$ is selected from the group consisting of -allyl, —$CH_3$, and —$CH_2CH_2CH_2OH$,
$R_2$ is selected from the group consisting of H, —$CH_2CO_2H$, —$CH_2CH_2OH$, —$CH_2CH_2CH_2OH$, —$CH_2CONH_2$, and —$CH_2CO_2Et$, and R<sub>3</sub> is selected from the group consisting of 4-substituted-2,6-dichloropyridine, 4-substituted-2-chloro-6-hydroxyethyl pyridine, 4-substituted-2-chloro-6-hydroxypropyl pyridine, 4-substituted-2-(aminoethyl)-6-chloro pyridine, 4-substituted-2-(aminoethylmethyl)-6-chloro pyridine, and 5-substituted-2,3-dichloro thiophene, with the proviso that $R_1$ is not —$CH_3$ if $R_2$ is H,
or any physiologically acceptable salts thereof.

2. The compound of claim 1, wherein:
$R_1$ is -allyl,
$R_2$ is H, and
$R_3$ is 4-substituted-2,6-dichloropyridine,
or any physiologically acceptable salts thereof.

3. The compound of claim 1, wherein:
$R_1$ is —$CH_3$,
$R_2$ is —$CH_2CH_2OH$, and
$R_3$ is 4-substituted-2,6-dichloropyridine,
or any physiologically acceptable salts thereof.

4. The compound of claim 1, wherein:
$R_1$ is —$CH_3$,
$R_2$ is —$CH_2CH_2OH$,
$R_3$ is 4-substituted-2-chloro-6-hydroxyethyl pyridine
or any physiologically acceptable salts thereof.

5. The compound of claim 1, wherein:
$R_1$ is —$CH_3$,
$R_2$ is —$CH_2CH_2OH$,
$R_3$ is 4-substituted-2-chloro-6-hydroxypropyl pyridine,
or any physiologically acceptable salts thereof.

6. A method of treating a subject suffering from lung fibrosis, the method comprising administering to the subject a therapeutically effective amount of the compound of claim 1.

7. A pharmaceutical composition comprising one or more physiologically acceptable carriers or excipients and a sphingosine-1-phosphate receptor 2 (S1P<sub>2</sub>) antagonist compound of the formula:

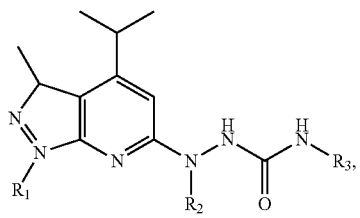

wherein:
$R_1$ is selected from the group consisting of -allyl, —$CH_3$, and —$CH_2CH_2CH_2OH$, $R_2$ is selected from the group consisting of H, —$CH_2CO_2H$, —$CH_2CH_2OH$, —$CH_2CH_2CH_2OH$, —$CH_2CONH_2$, and —$CH_2CO_2Et$, and $R_3$ is selected from the group consisting of 4-substituted-2,6-dichloropyridine, 4-substituted-2-chloro-6-hydroxyethyl pyridine, 4-substituted-2-chloro-6-hydroxypropyl pyridine, 4-substituted-2-(aminoethyl)-6-chloro pyridine, 4-substituted-2-(aminoethylmethyl)-6-chloro pyridine, and 5-substituted-2,3-dichloro thiophene, with the proviso that $R_1$ is not —$CH_3$ if $R_2$ is H,
or any physiologically acceptable salts thereof.

8. The pharmaceutical composition of claim 7, wherein:
$R_1$ is -allyl,
$R_2$ is H, and
$R_3$ is 4-substituted-2,6-dichloropyridine.

9. The pharmaceutical composition of claim 7, wherein:
$R_1$ is —$CH_3$,
$R_2$ is —$CH_2CH_2OH$, and
$R_3$ is 4-substituted-2-chloro-6-hydroxyethyl pyridine.

10. The pharmaceutical composition of claim 7, further comprising an additional pharmacological agent selected from the group consisting of cytotoxic agents, hormones, non-steroidal anti-inflammatory drugs (NSAIDs), and any mixtures thereof.

11. The pharmaceutical composition of claim 7, further comprising a steroidal anti-inflammatory drug.

12. The pharmaceutical composition of claim 7, wherein the pharmaceutical composition is formulated for administration by a route selected from the group consisting of inhalational, insufflation, oral, buccal, parenteral and rectal.

13. The pharmaceutical composition of claim 8, wherein the pharmaceutical composition is formulated for administration by a route selected from the group consisting of inhalational, insufflation, oral, buccal, parenteral and rectal.

14. The pharmaceutical composition of claim 7, further comprising a chemotherapeutic agent.

* * * * *